United States Patent [19]
Sabol et al.

[11] Patent Number: 6,017,923
[45] Date of Patent: Jan. 25, 2000

[54] CARBO-ACYCLIC NUCLEOSIDE DERIVATIVES AS ANTIVIRAL AND ANTINEOPLASTIC AGENTS

[75] Inventors: Jeffrey S. Sabol, Loveland, Ohio; Sai P. Sunkara, San Diego, Calif.; Shawn C. Miller, Indianapolis, Ind.

[73] Assignee: Hoechst Marion Roussel, Inc., Bridgewater, N.J.

[21] Appl. No.: 08/564,296

[22] Filed: May 31, 1996

Related U.S. Application Data

[63] Continuation-in-part of application No. 08/081,727, Jun. 23, 1993, abandoned.

[51] Int. Cl.[7] .......... A61K 31/52; C07D 473/18
[52] U.S. Cl. .......... 514/262; 544/276; 544/265; 544/277; 544/264; 544/314; 544/317; 544/318; 546/118; 546/119; 548/307.4; 548/309.7; 548/310.1; 548/310.4; 548/304.4; 514/274; 514/261; 514/262; 514/303; 514/394; 514/395; 514/300
[58] Field of Search .................. 544/276, 265, 544/277, 264, 317, 318; 546/119; 548/307.4, 309.7, 310.1, 310.4, 304.4; 514/274, 261, 262, 300, 303, 394, 395

[56] References Cited

U.S. PATENT DOCUMENTS

| | | | |
|---|---|---|---|
| 4,199,575 | 4/1980 | Gunther et al. | 424/217 |
| 4,221,794 | 9/1980 | Simon et al. | 425/253 |
| 4,355,032 | 10/1982 | Verheyden et al. | 424/253 |
| 4,798,833 | 1/1989 | Johansson et al. | 514/262 |
| 4,935,427 | 6/1990 | Border et al. | 514/261 |
| 5,043,339 | 8/1991 | Beauchamp | 514/274 |

FOREIGN PATENT DOCUMENTS

| | | |
|---|---|---|
| 0146516 | 12/1984 | European Pat. Off. |
| 8906235 | 12/1988 | WIPO. |

OTHER PUBLICATIONS

Bestman, et al., Agnew Chem. Int. Ed. Engl 29:(1):99–100 (1990).
McCarthy, et al., Tetrahedron Letters 31(38):5449–5452 (1990).
Edwards, et al., Tetrahedron Letters 31(39):5571–5574 (1990).
McCarthy, et al., J. Am. Chem. Soc. 113:7439–7441 (1991).
Ziegler, et al., J. Am. Chem. Soc. 115:2581–2589 (1993).
Mori, et al., Tetrahedron, 35:933–940 (1979).
Chan, et al., J. Org. Chem. 43(8): 1526–32 (1978).
Speziale, et al., J. Am. Chem. Soc. 84:854–859 (1962).
Chu, et al., J. Heterocycl Chem. 23:289–317 (3/4, 1986).
Brown, et al., Synthetic Procedures in Nucleic Acid Chemistry, vol. 1 (Zorbach & Tipson eds.), pp. 98–99.
Overberger, et al., Tetrahedron Letters, 30(1):51–54 (1989).

*Primary Examiner*—Jose'G. Dees
*Assistant Examiner*—Sabiha N. Qazi
*Attorney, Agent, or Firm*—Mark C. Nelligan

[57] ABSTRACT

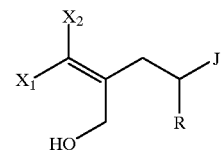

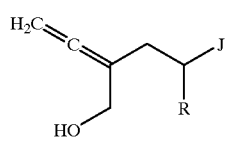

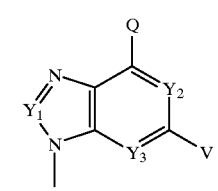

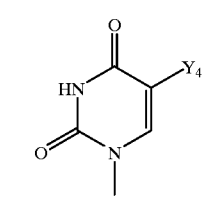

The present invention is directed to a class of novel carbocyclic derivatives having formulas (I) and (II) and their use as anti-viral and anti-neoplastic agents, wherein $X_1$ and $X_2$ are each independently hydrogen, fluorine, or chlorine, R is hydrogen or hydroxymethyl, J is a radical of formulas (a), (b) and (c). $Y_1$ is a CH group, a CCl group, a CBr group or a $CNH_2$ group, $Y_2$ and $Y_3$ are each independently nitrogen or a CH group, $Y_1$ is a CH group, a CCl group, a CBr group or a $CNH_2$ group, $Y_2$ and $Y_3$ are each independently nitrogen or a CH group, $Y_4$ is hydrogen, $C_1$–$C_4$ alkyl, $C_1$–$C_4$ alkoxy or halogen, $Y_5$ is $NH_2$ or $C_1$–$C_4$ alkoxy, Q is $NH_2$, NHOH, $NHCH_3$, OH, or hydrogen, and V is hydrogen, halogen or $NH_2$; or a pharmaceutically acceptable salt thereof.

26 Claims, No Drawings

CARBO-ACYCLIC NUCLEOSIDE DERIVATIVES AS ANTIVIRAL AND ANTINEOPLASTIC AGENTS

The present application has an effective international filing date of May 31, 1994 as application PCT/US94/06119 which designated the U.S. and entered the U.S. national phase on Dec. 19, 1995 under 35 U.S.C. 371 and was assigned Ser. No. 08/564,296, which is a continuation-in-part of application Ser. No. 08/081,727 filed on Jun. 23, 1993, now abandoned.

The present invention relates to novel carbo-acyclic derivatives that are useful as anti-viral and anti-neoplastic agents.

The present invention provides novel carbo-acyclic nucleoside derivatives of formula:

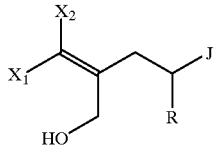
(Formula I)

wherein $X_1$ and $X_2$ are each independently hydrogen, fluorine, or chlorine,

R is hydrogen or hydroxymethyl,

J is a radical of the formula

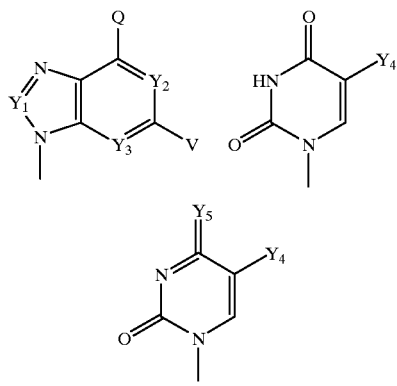

$Y_1$ is a CH group, a CCl group, a CBr group or a $CNH_2$ group, $Y_2$ and $Y_3$ are each independently nitrogen or a CH group, $Y_4$ is hydrogen, $C_1$–$C_4$ alkyl, $C_1$–$C_4$ alkoxy or halogen, $Y_5$ is $NH_2$ or $C_1$–$C_4$ alkoxy, Q is $NH_2$, NHOH, $NHCH_3$, OH, or hydrogen, and V is hydrogen, halogen or $NH_2$;

or a pharmaceutically acceptable salt thereof.

In addition, the present invention provides novel carbo-acyclic nucleosides of formula:

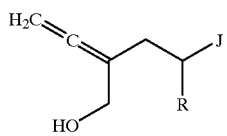
(Formula II)

wherein

R is hydrogen or hydroxymethyl,

J is a radical of the formula

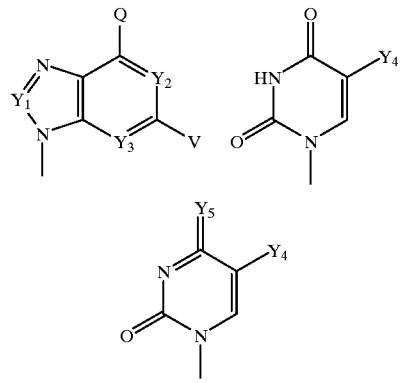

$Y_1$ is a CH group, a CCl group, a CBr group or a $CNH_2$ group, $Y_2$ and $Y_3$ are each independently nitrogen or a CH group, $Y_4$ is hydrogen, $C_1$–$C_4$ alkyl, $C_1$–$C_4$ alkoxy or halogen, $Y_5$ is $NH_2$ or $C_1$–$C_4$ alkoxy, Q is $NH_2$, NHOH, $NHCH_3$, OH, or hydrogen, and V is hydrogen, halogen or $NH_2$;

or a pharmaceutically acceptable salt thereof.

Another embodiment of the present invention is a method of treating a patient afflicted with a neoplastic disease state or of controlling the growth of a neoplasm in a patient afflicted with a neoplastic disease state comprising administration of a therapeutically effective antineoplastic dose of a compound of Formulas I or II.

A further embodiment of the present invention is a method of treating a patient afflicted with a viral infection or of controlling a viral infection in a patient afflicted therewith comprising administration of a therapeutically effective antiviral amount of a compound of Formulas I or II.

DETAILED DESCRIPTION OF THE INVENTION

As used herein, the term "Pg" refers to a protecting group. The protecting group, herein delineated $Pg_1$, $Pg_2$, $Pg_3$, $Pg_4$, $Pg_5$, can be conventional hydroxy protecting groups. The selection and utilization of particular protecting groups is well known to one of ordinary skill in the art. In general, protecting groups should be selected which adequately protect the functionality in question during the subsequent synthetic steps and which are readily removable under conditions that do not cause degradation of the desired product.

As used herein, the designation "∼∼∼" refers to a bond for which the stereochemistry is not designated.

As used herein, the terms "hydroxymethyl" and "hydroxymethyl group" refers to a —$CH_2OH$ radical.

As used herein, the term "$C_1$–$C_6$ alkyl" refers to a saturated hydrocarbon radical of from one to six carbon atoms of straight, branched, or cyclic configuration and includes methyl, ethyl, propyl, isopropyl, n-butyl. isobutyl. n-pentyl, n-hexyl, cyclopentyl, cyclohexyl, and the like.

As used herein, the term "halogen" or "halo-" refers to a fluorine, chlorine, bromine, or iodine atom.

As used herein, the term "nitrogen" refers to a trivalent nitrogen atom attached to two radicals.

As used herein, the term "$C_1$–$C_4$ alkyl" refers to a saturated, straight or branched chain, hydrocarbon radical of one to four carbon atoms and includes methyl, ethyl, propyl, isopropyl, n-butyl, isobutyl, t-butyl and the like.

As used herein, the term "$C_1$–$C_4$ alkoxy" refers to a $C_1$–$C_4$ alkyl bearing an oxy group and includes methoxy, ethoxy, propoxy, butoxy and the like.

As used herein, the term "nucleoside base" refers to a radical of formula J as described above.

As used herein, the term "protected nucleoside base" refers to a nucleoside base which contains a protecting group which reduces the number of reactive sights, such as $N^6$-benzoyladenine, $O^2$, $O^4$-bis(trimethylsilyl)uracil, $O^2$, $O^4$-bis(methyl)uracil, $N^6$-acetylcytosine, $N^2$-acetyl-$O^6$-diphenylcarbamoylguanine, $O^2$, $N^4$-bis(trimethylsilyl) cytosine, $N^6$, $N^6$-bis(benzoyl)adenine, 4-ethoxypyrimidin-2-one, and the like.

As used herein, the term "masked nucleoside base" refers to a nucleoside base which upon modification is converted to a nucleoside base, such as 6-chloropurine, 2,6-dichloropurine, 2-amino-6-chloropurine, 6-iodopurine, 6-iodo-2-chloropurine, 4-ethoxypyrimidin-2-one, 6-iodouracil, 6-bromouracil, and the like.

As used herein, the term "pharmaceutically acceptable addition salt refers to either an acid addition salt or a basic addition salt.

The expression "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, and sulfonic acids such as p-toluenesulfonic acid, methanesulfonic acid and 2-hydroxyethane sulfonic acid. Either the mono- or di-acid salts may be formed, and such salts may exist in either a hydrated or substantially anhydrous form.

The expression "pharmaceutically acceptable basic addition salts" is intended to apply to any non-toxic organic or inorganic basic addition salts of the compounds represented by Formula I or Formula II or any of its intermediates. Illustrative bases which form suitable salts include alkali metal or alkaline-earth metal hydroxides such as sodium, or potassium, and aliphatic or alicyclic amines, such as methylamine, dimethylamine, or trimethylamine. Either the mono- or di-basic salts may be formed with those compounds.

Compounds of Formula I and Formula II in which R is hydroxymethyl exist as optical isomers. Any reference in this application to one of the compounds represented by Formula I and Formula II is meant to encompass either a specific optical isomer or a mixture of optical isomers. The specific optical isomers can be separated and recovered by techniques known in the art such as chromatography on chiral stationary phases, or ester formation with a chiral acid followed by separation of the resultant diastereomeric esters and hydrolysis to the desired optical isomer.

Compounds of Formula I and Formula II exist as geometric isomers. Any reference in this application to one of the compounds represented by Formula I and Formula II is meant to encompass either a specific geometric isomer or a mixture of geometric isomers. The specific geometric isomers can be separated and recovered by techniques known in the art such as chromatography on silica gel or chromatography on ion exchange resins.

Illustrative Examples of compounds encompassed by the present invention include:

(E)-4-(Adenin-9-yl)-2-hydroxymethyl-1-fluorobut-1-ene, (Z)-4-(Adenin-9-yl)-2-hydroxymethyl-1-fluorobut-1-ene, 4-(Adenin-9-yl)-2-hydroxymethylbut-1-ene, (E)-4-(Cytosin-1-yl)-2-hydroxymethyl-1-fluorobut-1-ene, 4-(Adenin-9-yl)-2-hydroxymethyl-1,1-dichlorobut-1-ene, (E)-4-(Adenin-9-yl)-2-hydroxymethyl-1-chlorobut-1-ene, (E)-4-(Urac-1-yl)-2-hydroxymethyl-1-fluorobut-1-ene, (Z)-4-(Adenin-9-yl)-2-hydroxymethyl-1-chlorobut-1-ene, 3-Hydroxymethyl-5-(urac-1-yl)pent-1,2-diene, (R)-3,5-Bis(hydroxymethyl)-5-(urac-1-yl)pent-1,2-diene, (S)-3,5-Bis(hydroxymethyl)-5-(urac-1-yl)pent-1,2-diene, 4-(Cytosin-1-yl)-2-hydroxymethylbut-1-ene, 4-(Cytosin-1-yl)-2-hydroxymethyl-1,1-dichlorobut-1-ene, (E)-4-(Cytosin-1-yl)-2-hydroxymethyl-1-chlorobut-1-ene, (R)-4-(Adenin-9-yl)-2,4-bis(hydroxymethyl)but-1-ene, (R)-4-(Adenin-9-yl)-2,4-bis(hydroxymethyl)-1,1-dichlorobut-1-ene, (1E,2R)-4-(Adenin-9-yl)-2,4-bis(hydroxymethyl)-1-fluorobut-1-ene, (S)-4-(Adenin-9-yl)-2,4-bis(hydroxymethyl)but-1-ene, (S)-4-(Adenin-9-yl)-2,4-bis(hydroxymethyl)-1,1-difluorobut-1-ene, (1E,2S)-4-(Adenin-9-yl)-2,4-bis(hydroxymethyl)-1-chlorobut-1-ene, 4-(Adenin-9-yl)-2-hydroxymethyl-1,1-difluorobut-1-ene, 4-(Cytosin-1-yl)-2-hydroxymethyl-1,1-difluorobut-1-ene, 4-(Urac-1-yl)-2-hydroxymethyl-1,1-difluorobut-1-ene, 3-Hydroxymethyl-5-(cytosin-1-yl)pent-1,2-diene, (R)-3,5-Bis(hydroxymethyl)-5-(cytosin-1-yl)pent-1,2-diene, (S)-3,5-Bis(hydroxymethyl)-5-(cytosin-1-yl)pent-1,2-diene, 3-Hydroxymethyl-5-(adenin-9-yl)pent-1,2-diene, (R)-3,5-Bis(hydroxymethyl)-5-(adenin-9-yl)pent-1,2-diene, (S)-3,5-Bis(hydroxymethyl)-5-(adenin-9-yl)pent-1,2-diene, 3-Hydroxymethyl-5-(4-ethoxy-2-oxo-pyrimid-1-yl)pent-1,2-diene, (R)-3,5-Bis(hydroxymethyl)-5-(4-ethoxy-2-oxo-pyrimid-1-yl)pent-1,2-diene, (S)-3,5-Bis(hydroxymethyl)-5-(4-ethoxy-2-oxo-pyrimid-1-yl)pent-1,2-diene, (E)-4-(Thymin-1-yl)-2-hydroxymethyl-1-fluorobut-1-ene, (Z)-4-(5-Iodouracal-1-yl)-2-hydroxymethyl-1-fluorobut-1-ene, 4-(5-Fluorourac-1-yl)-2-hydroxymethylbut-1-ene.

Compounds of Formula I can be prepared as described in Scheme A. All the substituents, unless otherwise indicated, are previously defined. The reagents and starting materials are readily available to one of ordinary skill in the art.

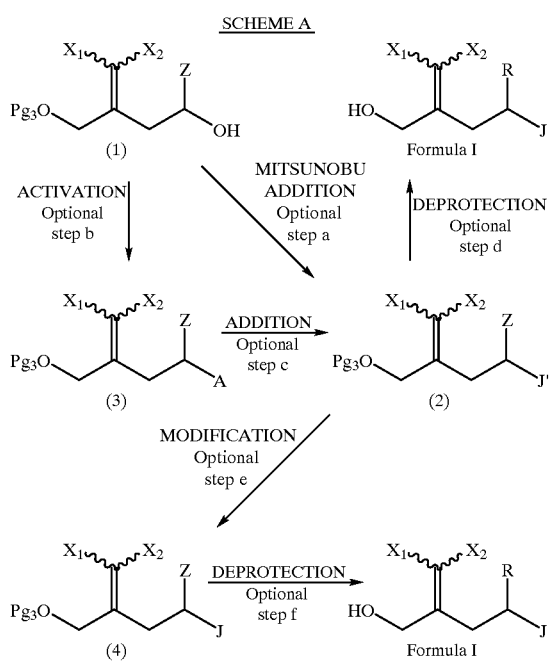

SCHEME A

In Scheme A Optional step a, a nucleoside base, a protected nucleoside base, or a masked nucleoside base is added by a Mitsunobu addition to an appropriate alcohol of structure 1 to form a carbo-acyclic nucleoside of structure 2: Bestmann, H. J.and Roth, D. *Angew. Chem. Inter. Ed. Engl.*, 29, 99–100, (1990); Toyota, A.; Katagiri, N.; Keneko, C. *Syn. Comm.*, 23, 1295–1305, (1993).

An appropriate alcohol of structure 1 is one in which Z is hydrogen in compounds which give final product of the Formula I in which R is hydrogen, and Z is a protected hydroxymethyl group, —CH$_2$OPg$_4$, in compounds which give final product of the Formula I in which R is hydroxymethyl.

For example, an alcohol of structure 1, is contacted with a molar equivalent of either a nucleoside base, a protected nucleoside base, or a masked nucleoside base and a molar equivalent of triphenylphosphine in a suitable solvent, such as tetrahydrofuran (THF). Diethyl azodicarboxylate neat or as a solution in a suitable solvent, such as tetrahydrofuran is added. After stirring for from 1–72 hours the product can be isolated and purified by techniques well known in the art. For example, the reaction mixture can be concentrated in vacuo to give a residue. The residue can be chromatographed on silica gel using a suitable organic eluent. The material obtained from chromatography can be recrystallized from a suitable solvent to give carbo-acyclic nucleosides of structure 2.

In Scheme A Optional step b, the position bearing the reactive hydroxyl of a compound of structure 1 can be activated by conversion to a suitable leaving group, -A.

A suitable leaving group is one that can be displaced by a nucleoside base, a protected nucleoside base, or a masked nucleoside base, such as the bromide, chloride, or methanesulfonate, with the methanesulfonate being preferred.

The activation of alcohols is well known and appreciated in the art. An appropriate alcohol of structure 1, as defined in step a above, can be converted to the chloride of structure 3, —A═—Cl. An appropriate alcohol of structure 1, is contacted with a molar equivalent of carbon tetrachloride and triphenylphosphine in a suitable solvent, such as carbon tetrachloride or dichloromethane. The chloride of structure 3, —A═—Cl, can be isolated and purified by techniques well known in the art, such as extraction, chromatography, recrystallization, and distillation.

Alternately, an appropriate alcohol of structure 1, as defined in step a above, can be converted to the bromide of structure 3, —A═—Br. An appropriate alcohol of structure 1, is contacted with a molar equivalent of carbon tetrabromide and triphenylphosphine in a suitable solvent, such as dichloromethane. The bromide of structure 3, —A═—Br, can be isolated and purified by techniques well known in the art, such as extraction, chromatography, recrystallization, and distillation.

Alternately, an appropriate alcohol of structure 1, as defined in step a above, is converted to the methanesulfonate of structure 3, —A═—OSO$_2$CH$_3$, by treatment with a molar equivalent of methanesulfonyl chloride in a suitable solvent, such as dichloromethane, acetonitrile, dimethylformamide, or pyridine. The reaction is carried out in the presence of a suitable base, such as triethylamine, pyridine, or diisopropylethylamine. Methanesulfonate of structure 3 can be isolated and purified by techniques well known in the art, such as extraction, chromatography, and recrystallization.

In Scheme A Optional step b, an activated compound of structure 3 is reacted with a nucleoside base, a protected nucleoside base, or a masked nucleoside base to give a compound of structure 2: Chu, C. K. and Cutler, S. J. *J. Hetercycl. Chem.*, 23, 289–317, (1986); *Synthetic Procedures in Nucleic Acid Chemistry* Vol.1 pg. 98–99 Zorbach, W. W., Tipson, R. S. eds; Overberger, C. G and Chang, J. Y. *Tet. Lets.* 30, 51–54, (1989).

For example, the compound of structure 3 are contacted with a molar equivalent of either a nucleoside base, a protected nucleoside base, or a masked nucleoside base in a suitable solvent, such as acetonitrile or dimethyl sulfoxide for compounds of structure 3 in which —A is bromide or chloride and dimethylformamide for compounds of structure 3 in which —A is methanesulfonate. The reaction may be carried out in the presence of a suitable base if needed, such as sodium bicarbonate, sodium carbonate, potassium carbonate, or sodium hydride. The protected carbo-acyclic nucleosides of the structure 2 can be isolated and purified as taught above for Scheme A, step a.

In Scheme A Optional step d, the compounds of structure 2 are deprotected to give compounds of Formula I. Optional step d is used for compounds 2 in which J' is the nucleoside base, J, desired in compound of Formula I. For a compound of structure 2 in which Z is hydrogen removal of protecting group Pg$_3$ gives a compound of Formula I. For compound of structure 3 in which Z is a protected hydroxymethyl, —CH$_2$OPg$_4$, the protecting groups Pg$_3$ and Pg$_4$ may require sequential removal to give a compound of Formula I. The removal of protecting groups and the removal of protecting groups in a sequential manner utilizing suitable protecting groups such as those described in *Protecting Groups in Organic Synthesis* by T. Greene is well known and appreciated by those skilled in the art. Compounds of Formula I can be isolated and purified by techniques well known in the art, such as extraction, chromatography, and recrystallization.

In Scheme A Optional step e, the protected nucleoside base or masked nucleoside base, J', of the compounds of structure 2 are deprotected or modified to give compounds of structure 4. Optional step e is used when it is desired to modify nucleoside base J', either by deprotection or modification of a masking group, to give compounds 4 in which J is the nucleoside base desired in the final compound of Formula I. The protecting groups for the nucleoside base of the compounds of structure 2 can be removed as described in *Protecting Groups in Organic Synthesis* by T. Greene as is well known and appreciated by those skilled in the art. The masking groups of the compounds of structure 2 can be modified to produce a nucleoside base, J. The masking groups used and the methods for their modification are well know to those of ordinary skill in the art. Compounds of structure 4 can be isolated and purified by techniques well known in the art, such as extraction, chromatography, and recrystallization.

In Scheme A Optional step f, the compounds of structure 4 are deprotected to give compounds of Formula I. For a compound of structure 4 in which Z is hydrogen removal of protecting group Pg3 gives a compound of Formula I. For compound of structure 4 in which Z is a protected hydroxymethyl, —$CH_2OPg_4$, the protecting groups Pg3 and $Pg_4$ may require sequential removal to give a compound of Formula I. The removal of protecting groups and the removal of protecting groups in a sequential manner utilizing suitable protecting groups such as those described in *Protecting Groups in Organic Synthesis* by T. Greene is well known and appreciated by those skilled in the art. Compounds of Formula I can be isolated and purified by techniques well known in the art, such as extraction, chromatography, and recrystallization.

The following examples present typical syntheses as described by Scheme A. These examples are understood to be illustrative only and is not intended to limit the scope of the present invention in any way. As used herein, the following terms have the meanings as indicated below: "g" refers to grams; "mL" refers to milliliters; "mg" refers to milligrams; "mmol" refers to millimoles; "° C." refers to degrees Celsius; "mp" refers to melting point; "M1" refers to molar concentration; "THF" refers to tetrahydrofuran; "MHz" refers to megahertz, "Hz" refers to Hertz, "DMSO" refers to dimethyl sulfoxide, "$d_6$ DMSO" refers to dimethyl sulfoxide hexadeuteride; "μL" refers to microliters; "$R_f$" refers to retention factor.

EXAMPLE 1
Scheme A, Optional step a: (E)-4-(6-Chloropurin-9-yl)-2-benzoyloxymethyl-1-fluorobut-1-ene Combine (E)-4-hydroxy-2-benzoyloxymethyl-1-fluorobut-1-ene (0.755 g, 3.37 mmol), triphenylphosphine (0.883 g, 3.37 mmol) and 6-chloropurine (0.52 g, 3.37 mmol) in anhydrous THF' (10 mL) and add dropwise diethyl azodicarboxylate (530 μL, 3.37 mmol). The reaction mixture is stirred for 48 hours and then concentrate in vacuo. Chromatograph on silica gel eluting with 1/1 ethyl acetate/hexane to give 0.57 g of the title compound as an oil. $^1$H NMR ($CDCl_3$, 300 MHz) δ2.91 (t, J=1.91 Hz, 2H), 4.53 (t, J=7.01 Hz, 2H), 4.79 (d, J=3.59 Hz, 2H), 6.79 (d, J=82.11 Hz, 1H), 7.45 (dd, J=7.34 Hz, 1.65 Hz, 2H), 7.56 (m, 1H), 8.05 (t, J=1.14 Hz, 1H), 8.69 (s, 1H); $^{19}$F NMR ($CDCl_3$, 282 MHz) δ -125.64 (d, J=82.11 Hz).

EXAMPLE 2
Scheme A, Optional step a: (Z)-4-(6-Chloropurin-9-yl)-2-benzoyloxymethyl-1-fluorobut-1-ene Combine (Z)-4-hydroxy-2-benzoyloxymethyl-1-fluorobut-1-ene (0.128 g, 0.572 mmol), triphenylphosphine (0.152 g , 0.572 mmol) and 6-chloropurine (0.0885 g, 0.572 mmol) in anhydrous THF (10 mL) and add diethyl azodicarboxylate (90 μL, 0.572 mmol). Stir the reaction mixture for 24 hours and then concentrate in vacuo. Chromatograph on silica gel eluting with 1/1 ethyl acetate/hexane to give 0.094 g of the title compound as a solid; mp; 87–88° C. Rf=0.24; silica gel, 1/1 ethyl acetate/hexane. $^1$H NMR ($CDCl_3$, 400 MHz) δ 2.68 (td, J=7.03 Hz, 3.41 Hz, 2H), 4.48 (t, J=7.13 Hz, 2H), 5.11 (s, 2H), 6.37 (d, J=81.77 Hz, 1H), 7.47 (t, J=8.15 Hz, 2H), 7.60 (td, J=7.68 Hz, 1.21 Hz, 1E), 8.06 (dd, J=8.15 Hz, 1.20 Hz, 1H), 8.70 (s, 1H); $^{19}$F ($CDCl_3$, 282 MHz) δ-123.55 (dt, J=81.77 Hz, 2.4 Hz).

EXAMPLE 3
Scheme A, Optional step a: (Z)-4-(6-Chloropurin-9-yl)-2-benzoyloxymethyl-1-chlorobut-1-ene Combine (Z)-4-hydroxy-2-benzoyloxymethyl-1-chlorobut-1-ene (4.8 mmol), triphenylphosphine (5.0 mmol) and 6-chloropurine (5.0 mmol) in anhydrous THF (20 mL) and add diethyl azodicarboxylate (790 μL, 5.0 mmol). Stir the reaction mixture for 24 hours and then concentrate in vacuo. Chromatograph on silica gel eluting with 1/1 ethyl acetate/hexane to give the title compound.

EXAMPLE 4
Scheme A, Optional step a: (E)-4-(6-Chloropurin-9-yl)-2-benzoyloxymethyl-1-chlorobut-1-ene Combine (E)-4-hydroxy-2-benzoyloxymethyl-1-chlorobut-1-ene (1.16 g, 4.82 mmol), triphenylphosphine (1.39 g, 5.3 mmol) and 6-chloropurine (0.819 g, 5.3 mmol) in anhydrous THF (20 mL) and add diethyl azodicarboxylate (835 μL, 5.3 mmol). Stir the reaction mixture for 24 hours and then concentrate in vacuo. Chromatograph on silica gel eluting with 1/1 ethyl acetate/hexane to give the title compound; $R_f$=0.60; silica gel, 1/1 ethyl acetate/hexane.

EXAMPLE 5
Scheme A, Optional step a: 4-(6-Chloropurin-9-yl)-2-benzoyloxvmethylbut-1-ene Combine 4-hydroxy-2-benzoyloxymethylbut-1-ene (0.565 g, 2.73 mmol), triphenylphosphine (0.719 g, 2.73 mmol) and 6-chloropurine (0.423 g, 2.73 mmol) in anhydrous THF (15 mL) and add diethyl azodicarboxylate (431 μL, 2.73 mmol). Stir the reaction mixture for 48 hours and then concentrate in vacuo. Chromatograph on silica gel eluting with 1/1 ethyl acetate/hexane to give the title compound as a solid. $R_f$=0.27; silica gel, 1/1 ethyl acetate/hexane. $^1$H NMR ($CDCl_3$, 300 MHz) δ2.77 (t, J=6.87 Hz, 2H), 4.53 (t, J=6.87 Hz, 2H), 4.87 (s, 2H), 4.89 (s, 2H), 5.21 (s, 1H), 7.47 (dd, J=4.44 Hz, 1.25 Hz, 2H), 7.59 (m, 1H), 8.04 (dd, J=4.44 Hz, 1.25 Hz, 1H), 8.15 (s, 1H), 8.73 (s, 1H).

EXAMPLE 6
Scheme A, Optional step a: (E)-4-(4-Ethoxypyrimidinone-1-yl)-2-benzoyloxymethyl-1-fluorobut-1-ene Combine (E)-4-hydroxy-2-benzoyloxymethyl-1-fluorobut-1-ene (1.12 g, 5.0 mmol), triphenylphosphine (1.31 g, 5.0 mmol) and 4-ethoxypyrimidinone (0.35 g, 2.5 mmol)[Hilbert, G. E. and Jansen, E. F. *JACS* 57, 552, (1935)] in anhydrous THF (50 mL) and add dropwise diethyl azodicarboxylate (0.45 g, 2.50 mmol). The reaction mixture is stirred for 24 hours and then concentrate in vacuo. Chromatograph on silica gel to give the title compound. $^1$H NMR ($CDCl_3$, 300 MHz) δ 1.35 (t, J=7.1 Hz, 3H), 2.59 (dt, J=3.0 Hz, 1.0 Hz, 2H), 4.35 (q, J=7.1 Hz, 2H), 5.03 (dd, J=3.0 Hz, 1.0 Hz, 2H), 6.31 (d, J=5.7 Hz, 1H), 6.65 (dd, J=83 Hz, 1.0 Hz, 1H), 7.43 (tt, J=7.4 Hz, 1.0 Hz, 2H), 7.55 (tt, J=7.4 Hz, 1.0 Hz, 1H), 8.02 (dt, J=7.4 Hz, 1.0Hz, 2H), 8.11 (d, J=5.7 Hz, 1H). 19F NMR ($CDCl_3$, 282 MHz) –127.08 (d, J=83 Hz).

EXAMPLE 7

Scheme A, Optional step b: (E)-4-[(Methanesulfonyl)oxy]-2-benzoyloxymethyl-1-fluorobut-1-ene Combine (E)-4-hydroxy-2-benzoyloxymethyl-1-fluorobut-1-ene (0.477 g, 1.99 mmol) and triethylamine (1.4 mL, 9.95 mmol) in anhydrous dichloromethane (5 mL). Cool in an ice bath. Add dropwise a solution of methanesulfonyl chloride (0.062 g, 0.61 mmol) in anhydrous dichloromethane (2 mL) and stir the reaction mixture for 1 hour in the ice bath. Apply the reaction mixture to a bed of silica gel and elute with 1/2 ethyl acetate/hexane to give the title compound. $R_f$=0.30; silica gel, 1/2 ethyl acetate/hexane. $^1$H NMR (CDCl$_3$, 300 MHz) δ2.72 (td, J=5.7 Hz, 2.1 Hz, 2H), 3.00 (s, 3H), 3.15 (s, 3H), 4.40 (t, J=6.84 Hz, 2H), 4.78 (dd, J=82.06 Hz, 0.82 Hz, 1H), 7.46 (td, J=8.12 Hz, 0.82 Hz, 2H), 7.59 (t, J=7.25, 1H), 8.03 (dd, J=8.48 Hz, 1.05 Hz, 2H). $^{19}$F NMR (CDCl$_3$, 282 MHz) −125.65 (d, J=82.06 Hz).

EXAMPLE 7a

Scheme A, Optional step b: (E)-4-Bromo-2-benzoyloxymethyl-1-fluorobut-1-ene

Combine (E)-4-hydroxy-2-benzoyloxymethyl-1-fluorobut-1-ene (0.448 g, 2.00 mmol) and triphenylphosphine (0.576 g, 2.20 mmol) in anhydrous dichloromethane (20 mL). Add dropwise N-bromosuccinimide (0.391 g, 2.20 mmol). After 18 hours, dilute the reaction mixture with dichloromethane (50 mL) and extract with water and a saturated aqueous solution of sodium chloride. Dry the organic layer over MgSO$_4$, filter, and evaporate in vacuo. Apply the reaction mixture to a bed of silica gel and elute with 1/9 ethyl acetate/hexane to give the title compound. $R_f$=0.27; silica gel, 1/19 ethyl acetate/hexane. $^1$H NMR (CDCl$_3$, 300 MHz) δ2.85 (t, J=7.0 Hz, 2H), 3.53 (t, J=7.0 Hz, 2H), 4.76 (dd, J=3.6 Hz, J=3.6 Hz 1.0 Hz, 2H), 6.88 (dt, J=82.5 Hz, 1.0 Hz, 1H), 7.46 (tt, J=7.0 Hz, 2.0 Hz, 2H), 7,56 (tt, J=7.0 Hz, 2.0 Hz, 1H), 8.04 (dt, J=7.0 Hz, 2.0 Hz, 2H). $^{19}$F NMR (CDCl$_3$, 282 MHz) −125.89 (d, J=82.5 Hz).

EXAMPLE 7b

Scheme A, Optional step b: (Z)-4-Bromo-2-benzoyloxymethyl-1-fluorobut-1-ene

Combine (Z)-4-hydroxy-2-benzoyloxymethyl-1-fluorobut-1-ene (0.455 g, 2.03 mmol) and triphenylphosphine (0.576 g, 2.20 mmol) in anhydrous dichloromethane (20 mL). Add dropwise N-bromosuccinimide (0.391 g, 2.20 mmol). After 18 hours, dilute the reaction mixture with dichloromethane (50 mL) and extract with water and a saturated aqueous solution of sodium chloride. Dry the organic layer over MgSO$_4$, filter, and evaporate in vacuo. Apply the reaction mixture to a bed of silica gel and elute with 1/9 ethyl acetate/hexane to give the title compound. $R_f$=0.38; silica gel, 1/19 ethyl acetate/hexane. $^1$H NMR (CDCl$_3$, 300 MHz) δ2.62 (td, J=6.8 Hz, 1.0 Hz, 2H), 4.99 (dd, J=28.0 Hz, 1.0 Hz, 2H), 7.46 (tt, J=7.0 Hz, 2.0 Hz, 2H), 7,59 (tt, J=7.0 Hz, 2.0 Hz, 1H), 8.04 (dt, J=7.0 Hz, 2.0 Hz, 2H). $^{19}$F NMR (CDCl$_3$, 282 MHz) −125.90 (d, J=82.5 Hz).

EXAMPLE 8

Scheme A, Optional step c: (E)-4-(Cytosin-1-yl)-2-benzoyloxymethyl-1-fluorobut-1-ene Combine cytosine (0.033 g, 0.30 mmol) and sodium hydride (0.012 g, 0.30 mmol, 60% in oil) in dimethylformamide (3 mL) and stir for 1 hour. Add (E)-4-[(methanesulfonyl)oxy]-2-benzoyloxymethyl-1-fluorobut-1-ene (0.091 g, 0.30 mmol) and stir for 24 hours. Evaporate in vacuo and chromatograph on silica gel to give the title compound.

EXAMPLE 8a

Scheme A, Optional step c: (E)-4-(4-Acetylaminopyrimidinone-1-yl )-2-benzoyloxymethyl-1-fluorobut-1-ene Combine N$^6$-acetylcytosine (0.106 g, 0.69 mmol) and potassium carbonate (0.105 g, 0.769 mmol) and (E)-4-bromo-2-benzoyloxymethyl-1-fluorobut-1-ene (0.198 g, 0.690 mmol) in dimethylformamide (10 mL). Heat in an oil bath at 80° C. and stir for 18 hour. Cool to ambient temperature and partition the reaction mixture between dichloromethane and a saturated aqueous solution of sodium bicarbonate. Separate the organic layer and dry over MgSO$_4$, filter and evaporate in vacuo to give a residue. Triturate with ethyl acetate and obtain a white solid. Filter and dry to give the title compound: mp 191–193° C. $R_f$=0.20; silica gel, 1/49 methanol/dichloromethane. $^1$H NMR (CDCl$_3$, 300 MHz) δ2.22 (s, 3H), 2.72 (td, J=6.6 Hz, 1.8 Hz, 2H), 4.08 (t, J=6.6 Hz, 1.8 Hz, 2H), 4.78 (d, J=4.0 Hz, 2H), 6.83 (d, J=82.2 Hz, 1H), 7.46 (tt, J=7.0 Hz, 2.0 Hz, 2H), 7.56 (tt, J=7.0 Hz, 2.0 Hz, 1H), 8.02 (dt, J=7.0 Hz, 2.0Hz, 2H). $^{19}$F NMR (CDCl$_3$, 282 MHz) −126.30 (d, J=82.2 Hz).

EXAMPLE 8b

Scheme A, Optional step c: (Z)-4-(4-Acetylaminopyrimidinone-1-yl)-2-benzoyloxymethyl-1-fluorobut-1-ene Combine N$^6$-acetylcytosine (0.282 g, 1.84 mmol) and potassium carbonate (0.280 g, 2.05 mmol) and (Z)-4-bromo-2-benzoyloxymethyl-1-fluorobut-1-ene (0.528 g, 1.84 mmol) in dimethylformamide (25 mL). Heat in an oil bath at 80° C. and stir for 18 hour. Cool to ambient temperature and partition the reaction mixture between dichloromethane and a saturated aqueous solution of sodium bicarbonate. Separate the organic layer and dry over MgSO$_4$, filter and evaporate in vacuo to give a residue. Triturate with ethyl acetate and obtain a white solid. Filter and dry to give the title compound: mp 203–204° C. $^1$H NMR (CDCl$_3$, 300 MHz) δ2.26 (s, 3H), 2.51 (td, J=6.1 Hz, 0.5 Hz, 2H), 4.03 (t, J=66.1 Hz, 1.8 Hz, 2H), 5.05 (d, J=3.0 Hz, 2H), 6.49 (d, J=82.6 Hz, 1H), 7.37 (d, J=7.2 Hz, 1H), 7.46 (tt, J=7.0 Hz, 2.0 Hz, 1H), 8.06 (dt, J=7.0 Hz, 2.0 Hz, 2H), 9.49 (bs, 1H). $^{19}$F NMR (CDCl$_3$, 282 MHz) −124.10 (d, J=82.6 Hz).

EXAMPLE 9

Scheme A, Optional step d: (E)-4-(Cytosin-1-yl)-2-hydroxymethyl-1-fluorobut-1-ene Combine (E)-4-(cytosin-1-yl)-2-benzoyloxymethyl-1-fluorobut-1-ene (0.050 g, 0.157 mmol), lithium hydroxide hydrate (6.6 mg. 0.157 mmol), methanol (3 mL), and water (0.5 mL) and stir for 8 hours. Evaporate in vacuo and chromatograph on silica gel to give the title compound.

EXAMPLE 10

Scheme A, Optional step d: (E)-4-(Urac-1-yl)-2-benzoyloxymethyl-1-fluorobut-1-ene Combine (E)-4-(4-ethoxypyrimidinone-1-yl)-2-benzoyloxymethyl-1-fluorobut-1-ene (2.00 mmol) and dichloromethane (100 mL) and add 20% hydrogen chloride/methanol (w/w) (25 mL). The reaction mixture is stirred for 24 hours and then concentrate in vacuo. Chromatograph on silica gel to give the title compound.

EXAMPLE 11

Scheme A, Optional step e and f: (E)-4-(Cytosin-1-yl)-2-hydroxymethyl-1-fluorobut-1-ene Combine (E)-4-(4-ethoxypyrimidinone-1-yl)-2-benzoyloxymethyl-1-fluorobut-1-ene (2.85 mmol) with methanol (30 mL) and cool in an ice bath. Bubble ammonia gas into the solution at a slow rate for 10 minutes. Seal the vessel and heat in an oil bath to 50° C. for 18 hours. Cool the reaction vessel in an ice bath before opening. Evaporate the solvent in vacuo. Chromatograph on silica gel to give the title compound.

EXAMPLE 11a

Scheme A, Optional step e and f: (E)-4-(Cytosin-1-yl)-2-benzoyloxymethyl-1-fluorobut-1-ene Combine (E)-4-(4-acetylaminopyrimidinone-1-yl)-2-benzoyloxymethyl-1-fluorobut-1-ene (0.284 g, 0.79 mmol) with methanol (20 mL) and cool in an ice bath. Bubble ammonia gas into the solution at a slow rate for 10 minutes. Seal the vessel and heat in an oil bath to 50° C. for 18 hours. Cool the reaction vessel in an ice bath before opening. Evaporate the solvent in vacuo. Chromatograph on silica gel eluting with 1/9 methanol/ dichloromethane to give the title compound: mp 136–138° C. Rf=0.20; silica gel, 1/49 methanol/ dichloromethane. $^1$H NMR (CD$_3$OD, 300 MHz) δ 2.56 (td, J=6.6 Hz, 2.0 Hz, 2H), 3.29 (t, J=6.6 Hz, 2H), 4.00 (dd, J=4.0 Hz, 1.0 Hz, 2H), 5.81 (d, J=7.1 Hz, 1H), 6.72 (d, J=84.6 Hz, 1H), 7.53 (d, J=7.1 Hz, 1H). $^{19}$F NMR (CD$_3$OD, 282 MHz) −133.346 (d, J=84.6 Hz).

EXAMPLE 11b

Scheme A, Optional step e and f: (Z)-4-(Cytosin-1-yl)-2-benzoyloxymethyl-1-fluorobut-1-ene Combine (Z)-4-(4-acetylaminopyrimidinone-1-yl)-2-benzoyloxymethyl-1-fluorobut-1-ene (0.100 g, 0.554 mmol) and aqueous sodium hydroxide (2 mL, 1% w/v) in methanol (8 mL). After 1.5 hours, evaporate the solvent in vacuo to obtain a residue. Chromatograph on silica gel eluting with 3/17 methanol/ dichloromethane to give the title compound: mp 121–125° C. R$_f$=0.23; silica gel, 3/17 methanol/ dichloromethane. $^1$H NMR (CD$_3$OD, 300 MHz) δ2.39 (td, J=6.8 Hz, 3.0 Hz, 2H), 3.89 (t, J=6.8 Hz, 2H), 4.24 (dd, J=3.0 Hz, 0.7 Hz, 2H), 5.83 (d, J=7.2 Hz, 1H), 6.40 (d, J=85.2 Hz, 1H), 7.52 (d, J=7.2 Hz, 1H).

EXAMPLE 12

Scheme A, Optional steps e and f: (E)-4-(Adenin-9-yl)-2-hydroxymethyl-1-fluorobut-1-ene Combine (E)-4-(6-chloropurin-9-yl)-2-benzoyloxymethyl-1-fluorobut-1-ene (0.576 g, 1.60 mmol) with methanol (15 mL) and cool in an ice bath. Bubble ammonia gas into the solution at a slow rate for 3 minutes. Seal the vessel and heat in an oil bath to 50° C. for 16 hours. Cool the reaction vessel in an ice bath before opening. Evaporate the solvent in vacuo. Chromatograph on silica gel eluting with 1/9 methanol/methylene chloride to give 0.205 g of the title compound; mp: 168–169° C. R$_f$=0.45; silica gel, 1/9 methanol/methylene chloride. $^1$H NMR (d$_6$ DMSO, 300 MHz) δ2.63 (td, J=6.67 Hz, 1.42 Hz, 2H), 3.87 (dd, J=4.14 Hz, 0.71 Hz, 2H), 4.28 (t, J=6.96 Hz, 2H), 4.95 (br s, 1H), 6.74 (d, J=85.9 Hz, 1H), 7.35 (s, 2H), 8.13 (s, 1H), 8.17 (s, 1H); $^{19}$F NMR (d$_6$ DMSO, 282 MHz) δ−135.37 (d, J=85.9 Hz).

EXAMPLE 13

Scheme A, Optional steps e and f: (Z)-4-(Adenin-9-yl)-2-hydroxymethyl-1-fluorobut-1-ene Combine (Z)-4-(6-chloropurin-9-yl)-2-benzoyloxymethyl-1-fluorobut-1-ene (0.3 mmol) with methanol (10 mL) and cool in an ice bath. Bubble ammonia gas into the solution at a slow rate for 3 minutes. Seal the vessel and place in an oil bath heated to 50° C. for 16 hours. Cool the reaction vessel in an ice bath before opening. Evaporate the solvent in vacuo. Chromatograph on silica gel eluting with 1/9 methanol/methylene chloride to give the title compound; mp: 173–174° C. R$_f$=0.23; silica gel, 1/9 methanol/methylene chloride. $^1$H NMR (d$_6$ DMSO, 300 MHz) δ4.11 (qd, J=2.76 Hz, 0.85 Hz, 2H), 4.27 (t, J=6.69 Hz, 2H), 4.95 (t, J=5.70 Hz, 1H), 6.35 (d, J=85.72 Hz, 1H), 7.17 (s, 2H), 8.09 (s, 1H), 8.14 (s, 1H); $^{19}$F (d$_6$ DMSO, 282 MHz) δ−131.04 (dt, J=85.72 Hz, 2.82 Hz).

EXAMPLE 14

Scheme A, Optional steps e and f: (Z)-4-(Adenin-9-yl)-2-hydroxymethyl-1-chlorobut-1-ene Combine (Z)-4-(6-chloropurin-9-yl)-2-benzoyloxymethyl-1-chlorobut-1-ene (2.0 mmol) with methanol (20 mL) and cool in an ice bath. Bubble ammonia gas into the solution at a slow rate for 3 minutes. Seal the vessel and place in an oil bath heated to 50° C. for 16 hours. Cool the reaction vessel in an ice bath before opening. Evaporate the solvent in vacuo. Recrystallize from ethanol/ethyl acetate to give the title compound; mp: 224–225° C. R$_f$=0.24; silica gel, 2/8 ethanol/ethyl acetate. $^1$H NMR (d$_6$ DMSO, 300 MHz) δ2.70 (t, J=6.4 Hz, 2H), 4.20 (dd, J=5.63 Hz, 1.10 Hz, 2H), 4.30 (t, J=6.84 Hz, 2H), 5.10 (t, J=5.51 Hz, 1H), 5.84 (s, 1H), 7.17 (s, 2H), 8.08 (s, 1H), 8.13 (s, 1H).

EXAMPLE 15

Scheme A, Optional steps e and f: (E)-4-(Adenin-9-yl)-2-hydroxymethyl-1-chlorobut-1-ene Combine (E)-4-(6-chloropurin-9-yl)-2-benzoyloxymethyl-1-chlorobut-1-ene (1.0 mmol) with methanol (10 mL) and cool in an ice bath. Bubble ammonia gas into the solution at a slow rate for 3 minutes. Seal the vessel and heat in an oil bath to 50° C. for 16 hours. Cool the reaction vessel in an ice bath before opening. Evaporate the solvent in vacuo. Chromatograph on silica gel eluting with 1/9 methanol/methylene chloride. Recrystallize from isopropanol to give the title compound; mp: 175–176° C. Elem. Anal. calcd. for C$_{10}$H$_{13}$N$_5$OCl: C, 47.34; H, 4.77; N, 27.61. Found: C, 47.45; H, 4.70; N, 27.77. R$_f$=0.28; silica gel, 1/9 methanol/methylene chloride. $^1$H NMR (d$_6$ DMSO, 300 MHz) δ2.72 (t, J=6.87 Hz 2H), 3.97 (dd, J=5.64 Hz, 1.30 Hz, 2H), 4.29 (t, J=6.74 Hz, 2H), 5.12 (t, J=5.54 Hz, 1H), 6.24 (s, 1H), 7.15 (s, 2N), 8.07 (s, 1H), 8.14 (s, 1H).

EXAMPLE 16

Scheme A, Optional steps e and f: 4-(Adenin-9-yl)-2-hydroxymethylbut-1-ene

Combine (6-chloropurin-9-yl)-2-benzoyloxymethylbut-1-ene (1.0 g, 2.9 mmol) with methanol (20 mL) and cool in an ice bath. Bubble ammonia gas into the solution at a slow rate for 3 minutes. Seal the vessel and place in an oil bath heated to 50° C. for 16 hours. Cool the reaction vessel in an ice bath before opening. Evaporate the solvent in vacuo. Chromatograph on silica gel eluting with 1/99 methanol/methylene chloride to give a residue. Recrystallize the residue from isopropanol/ methanol to give the title compound; mp: 225–226° C. R$_f$=0.31; silica gel, 1/9 methanol/methylene chloride. $^1$H NMR (d$_6$ DMSO, 300 MHz) δ2.56 (t, J=7.57 Hz, 2H), 3.91 (d, J=5.47, 2H), 4.27 (t, J=7.19 Hz, 2H), 4.67 (s, 1H), 4.88 (t, J=5.63 Hz, 2H), 4.94 (d, J=1.47 Hz, 1H), 7.16 (s, 1H), 8.11 (s, 1H), 8.14 (s, 1H).

Compounds of Formula II can be prepared as described in Scheme B. All the substituents, unless otherwise indicated, are previously defined. The reagents and starting materials are readily available to one of ordinary skill in the art.

13

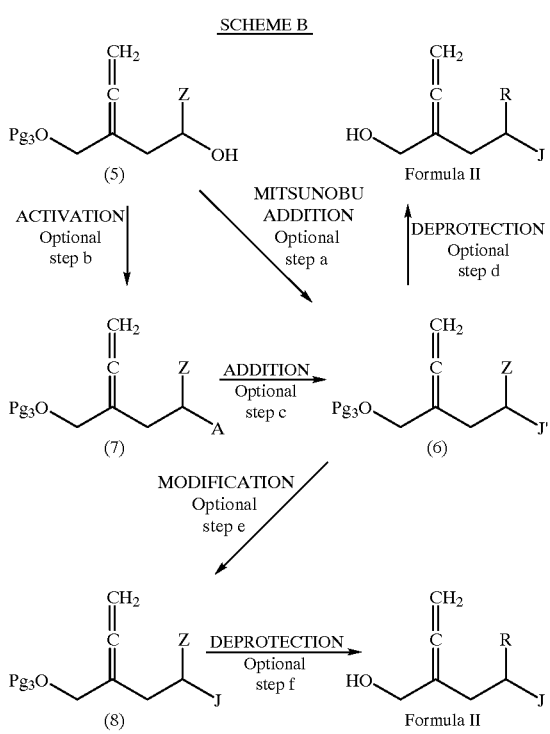

SCHEME B

In Scheme B Optional step a, the Mitsunobu addition may be carried out on the alcohol of structure 5 to give carboacyclic nucleoside of structure 6 as taught for the Mitsunobu addition in Scheme A Optional step a.

In Scheme B Optional step b, the position bearing the reactive hydroxyl of the alcohol of structure 5 can be activated by conversion to leaving group —A, by formation of the bromide, chloride, or methanesulfonate as taught in Scheme A Optional step b, to give compound of structure 7.

In Scheme B Optional step c, the leaving group —A of activated compounds of structure 7 can be displaced by a nucleoside base, a protected nucleoside base, or a masked nucleoside base as taught in Scheme A Optional step c, to give protected carbo-acyclic nucleoside of structure 6.

In Scheme B Optional step d, carbo-acyclic nucleoside of structure 6 is deprotected to give compounds of Formula II as taught in Scheme A Optional step d. This step is used for compound 6 in which J' is the nucleoside base, J, desired in compound of Formula II. For a compound of structure 6 in which Z is hydrogen removal of protecting group $Pg_3$ gives a compound of Formula II. For compound of structure 6 in which Z is a protected hydroxymethyl, —$CH_2OPg_4$, the protecting groups $Pg_3$ and $Pg_4$ may require sequential removal to give a compound of Formula II. The removal of protecting groups and the removal of protecting groups in a sequential manner utilizing suitable protecting groups such as those described in *Protecting Groups in Organic Synthesis* by T. Greene is well known and appreciated by those skilled in the art.

In Scheme B Optional step e, the protected or masked nucleoside base, J', of the compounds of structure 6 are modified to give compounds of structure 8. This is done as taught in Scheme A Optional step e. Optional step e is used when it is desired to modify nucleoside base J', either by deprotection or modification of a masking group, to give compounds 8 in which J is the nucleoside base desired in compound of Formula II. The protecting groups on the nucleoside base of the compounds of structure 8 can be removed as described in *Protecting Groups in Organic Synthesis* by T. Greene as is well known and appreciated by those skilled in the art. The masking groups of the compounds of structure 6 can be modified to produce a nucleoside base. The masking groups used and the methods for their modification are well know to those of ordinary skill in the art.

In Scheme B Optional step f, the compounds of structure 8 are deprotected to give compounds of Formula II. This is done as taught in Scheme A Optional step f. For a compound of structure 8 in which Z is hydrogen removal of protecting group $Pg_3$ gives a compound of Formula II. For compound of structure 8 in which Z is a protected hydroxymethyl, —$CH_2OPg_4$, the protecting groups $Pg_3$ and $Pg_4$ may require sequential removal to give a compound of Formula II. The removal of protecting groups and the removal of protecting groups in a sequential manner utilizing suitable protecting groups such as those described in *Protecting Groups in Organic Synthesis* by T. Greene is well known and appreciated by those skilled in the art.

The following examples present typical syntheses as described by Scheme B. These examples are understood to be illustrative only and is not intended to limit the scope of the present invention in any way. As used herein, the following terms have the meanings as indicated below: "g" refers to grams; "mL" refers to milliliters; "mg" refers to milligrams; "mmol" refers to millimoles; "° C." refers to degrees Celsius; "mp" refers to melting point;"M" refers to molar concentration; "$R_f$" refers to retention factor.

EXAMPLE 17

Scheme B, Optional step a: 5-(6-chloropurin-1-yl)-3-benzoyloxymethylpent-1,2-diene Combine 5-hydroxy-3-benzoyloxymethylpent-1,2-diene (1.0 mmol), triphenylphosphine (1.0 mmol) and 6-chloropurine (1.0 mmol) in anhydrous THF (20 mL) and add diethyl azodicarboxylate (1.0 mmol). Stir the reaction mixture for 24 hours and then concentrate in vacuo. Chromatograph on silica gel to give the title compound.

EXAMPLE 18

Scheme B, Optional step b: 5-chloro-3-benzoyloxymethylpent-1,2-diene

Combine 5-hydroxy-3-benzoyloxymethyl-pent-1,2-diene (0.5 mmol) and triphenylphosphine (0.5 mmol) in carbon tetrachloride and stir the reaction mixture for 24 hours. Concentrate in vacuo and chromatograph to give the title compound.

EXAMPLE 19

Scheme B, Optional step c: 5-(thymin-1-yl)-3-benzoyloxvmethylpent-1,2-diene

Combine thymine (2.25 mmol) and dimethyl sulfoxide (4 mL). Add 5-chloro-3-benzoyloxymethylpent-1,2-diene (0.50 mmol) and potassium carbonate (2.5 mmol). Stir the reaction mixture for 24 hours at room temperature. Filter and evaporate the dimethyl sulfoxide in vacuo to obtain a residue. Partition the residue between chloroform and water and extract the aqueous layer three times with chloroform. Dry the combined organic layers over $MgSO_4$ and concentrate in vacuo. Chromatograph to give the title compound.

EXAMPLE 20

Scheme B, Optional step d: 5-(thymin-1-yl)-3-hydroxymethylpent-1,2-diene

Combine 5-(thymin-1-yl)-3-benzoyloxymethylpent-1,2-diene (0.15 mmol), lithium hydroxide hydrate (0.15 mmol), methanol (3 mL), and water (0.5 mL) and stir for 8 hours. Partition the reaction mixture between ethyl acetate and 0.5 M sodium hydroxide solution, extract the aqueous layer with ethyl acetate, dry the combined organic layers over $MgSO_4$, and evaporate in vacuo. Chromatograph on silica gel to give the title compound.

EXAMPLE 21

Scheme B, Optional steps e and f: 5-(adenin-9-yl)-3-hydroxymethylpent-1,2-diene

Combine 5-(6-chloropurin-1-yl)-3-benzoyloxymethylpent-1,2-diene (0.60 mmol) with methanol (5 mL) and cool in an ice bath. Bubble ammonia gas into the solution at a slow rate for 3 minutes. Seal the vessel and heat in an oil bath to 50° C. for 16 hours. Cool the reaction vessel in an ice bath before opening. Evaporate the solvent in vacuo. Chromatograph on silica gel to give the title compound.

Scheme C illustrates the preparation of starting materials for Scheme A which afford compounds of Formula I in which $X_1$ and $X_2$ are hydrogen and fluorine and $X_2$ and $X_2$ are fluorine and hydrogen. All the substituents, unless otherwise indicated, are previously defined. The reagents and starting materials are readily available to one of ordinary skill in the art.

In Scheme C step a, ketone of structure 9 is converted to phenylsulfonylfluoroolefin of structure 10.

For example, ketone 9 is contacted with a slight excess of lithium diethyl (phenylsulfonyl)fluoromethylphosphonate, this methodology well known and appreciated in the art [J. R. McCarthy et al; *Tet. Let.* 31, 5449–5452, (1990); J. R. McCarthy et al; JACS 113, 7439–4740, (1991)]. The reaction is carried out in a suitable solvent, such as THF. The reaction is performed at temperatures from −78° C. to the refluxing temperature of the solvent. The phenylsulfonylfluoroolefin of structure 10 can be isolated and purified by techniques well known in the art, such as extraction, chromatography, and recrystallization.

Protecting groups used for ketone 9 are well known and appreciated in the art. For ketones of structure 9 in which Z is a protected hydroxymethyl, —$CH_2OPg_5$, the protecting groups $Pg_1$ and $Pg_5$ are together an acetonide.

In Scheme C step b, phenylsulfonyl group of compound of structure 10 is replaced with a trialkyltin group to give compound of structure 11.

This is accomplished by techniques well known in the art, such as reacting compound 10 with two molar equivalents of trialkyltin hydride reagent in the presence of 2,2'-azobisisobutyronitrile (AIBN). The three alkyl radicals of the trialkyltin group are $C_1$–$C_6$ alkyl groups. The reaction is

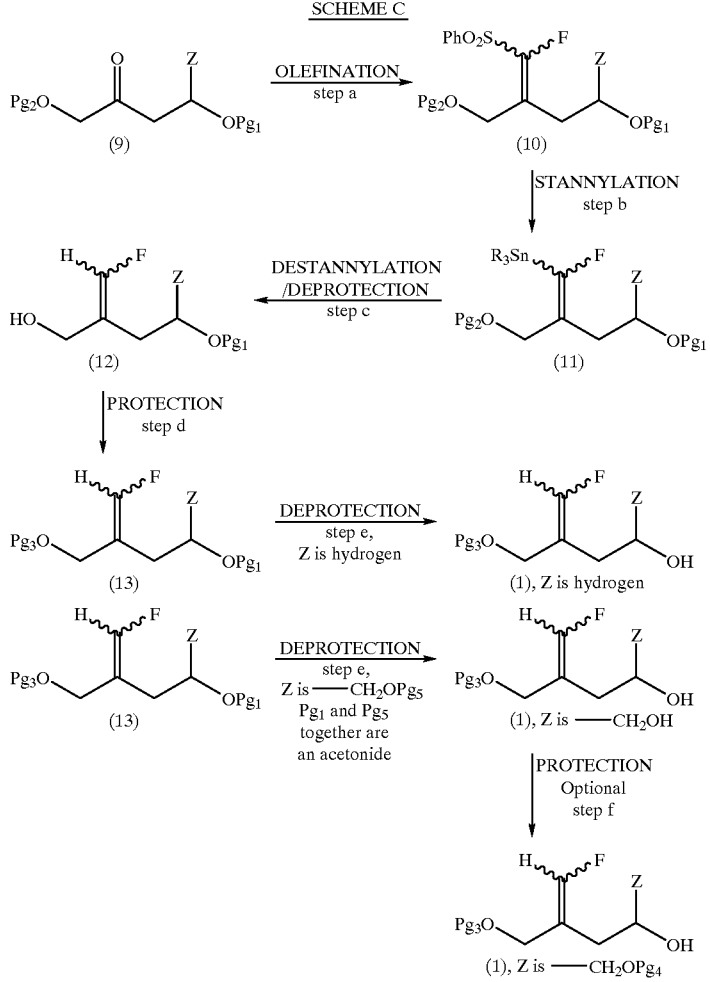

carried out at the refluxing temperature of a suitable solvent, such as benzene, cyclohexane, or hexane. Compound of the structure 11 can be isolated and purified by techniques well known in the art, such as extraction, chromatography, and recrystallization.

In Scheme C step c, the trialkyltin group and the fluoride labile protecting group $Pg_1$ of structure 11 are removed to give the fluoroolefin alcohol of structure 12.

For example, compound of structure 11 is contacted with a two equivalents of a suitable fluoride containing reagent, such as potassium fluoride, tetrabutylammonium fluoride, or cesium fluoride with tetrabutylammonium fluoride being preferred. The reaction is carried out in a solvent, such as methanol, tetrahydrofuran, ethanol, or isopropanol with tetrahydrofuran being preferred. The reaction is carried out at a temperature from room temperature to the reflux temperature of the solvent with room temperature being the preferred temperature when tetrahydrofuran is the solvent. Compound of the structure 12 can be isolated by extraction. The geometric isomers of compound 12 can be separated and purified by techniques well known in the art, such as chromatography and recrystallization.

In Scheme C step d, the reactive hydroxyl of fluoroolefin alcohol 12 is protected to give protected fluoroolefin of structure 13.

For example, fluoroolefin alcohol 12 is contacted with a suitable protecting group forming reagent. The reaction is typically carried out in a solvent at a temperature between −60° C. and the refluxing temperature of the solvent. The selection and use of protecting groups as described in *Protecting Groups in Organic Synthesis* by T. Greene is well known and appreciated by those skilled in the art. The protected fluoroolefin of structure 13 can be isolated and purified by techniques well known in the art, such as extraction, chromatography, and recrystallization.

In Scheme C step e, for compounds of structure 13 in which Z is hydrogen the protecting group $Pg_1$ of protected fluoroolefin 13 is removed to give fluoroolefin of structure 1 in which Z is hydrogen to be used to prepare final products of Formula I and II in which R is hydrogen.

The removal of protecting groups in a selective manner utilizing suitable protecting groups such as those described in *Protecting Groups in Organic Synthesis* by T. Greene is well known and appreciated by those skilled in the art. Compounds of structure 1 can be isolated and purified by techniques well known in the art, such as extraction, chromatography, and recrystallization.

In Scheme C step e, for compounds of structure 13 in which Z is a protected hydroxymethyl, —CH$_2$OPg$_5$, the protecting groups $Pg_1$ and $Pg_5$ are together an acetonide the deprotection gives a fluoroolefin diol of structure 13 in which Z is a hydroxymethyl group, —CH$_2$OH, which contains a primary hydroxyl group.

For example, compound of structure 13 is contacted with a suitable aqueous acid, such as acetic acid, for 1 hour to 24 hours. The product is obtained by techniques well known in the art. For example, concentrating the reaction mixture in vacuo and purifying the residue obtained by chromatography on silica gel.

In Scheme C Optional step f, the compound of structure 13 in which Z is a hydroxymethyl group, —CH$_2$OH, which contains a primary hydroxyl group, the primary hydroxyl group selectively protected with a suitable protecting group by techniques well known in the art and described in *Protecting Groups in Organic Synthesis* by T. Greene to give a fluoroolefin of structure 1 in which Z is a protected hydroxymethyl group, —CH$_2$OPg$_4$, to be used to prepare final products of Formula I and II in which R is hydroxymethyl.

The following example presents a typical synthesis as described by Scheme C. This example is understood to be illustrative only and is not intended to limit the scope of the present invention in any way. As used herein, the following terms have the meanings as indicated below: "g" refers to grams; "mL" refers to milliliters; "mg" refers to milligrams; "mmol" refers to millimoles; "IC" refers to degrees Celsius; "Imp" refers to melting point; "THF" refers to tetrahydrofuran; "AIBN" refers to 2,2'-azobisisobutyronitrile; "M" refers to molar; "$R_f$" refers to retention factor.

EXAMPLE 22

Scheme C, step a: (E) and (Z)-4-(p-Methoxybenzyloxy)-2-(t-butyldimethylsilyloxymethyl)-1-fluoro-1-phenylsulfonylbut-1-ene Combine diethyl [(phenylsulfonyl)fluoromethyl]phosphonate (17.19 mmol) with THF (120 mL) and cool to 0° C. before adding dropwise a solution of lithium hexamethyldisilazide (21 mL, 17.19 mmol). After 1 hour, add 4-(p-methoxybenzyloxy)-1-(t-butyldimethylsilyloxy)butan-2-one (4.85 g, 14.33 mmol) as a solution in THF (20 mL). Remove the cooling bath, stir the mixture for 15 minutes at room temperature and then reflux for 45 minutes. Partition the cooled mixture between diethyl ether and water, wash the separated ether layer with water, saturated sodium chloride solution and dry over MgSO$_4$. Concentrate in vacuo. Chromatograph on silica gel eluting with 1/9 ethyl acetate/hexane to give 5.01 g of the title compound as a yellow oil.

EXAMPLE 23

Scheme C, step b: (E) and (Z)-4-(p-Methoxybenzyloxy)-2-(t-butyldimethylsilyloxymethyl)-1-fluoro-1-tri-n-butylstannylbut-1-ene Combine 4-(p-methoxybenzyloxy)-2-(t-butyldimethylsilyloxymethyl)-1-fluoro-1-phenylsulfonylbut-1-ene (13.0 g, 26.28 mmol), tri-n-butyltin hydride (14.0 mL, 52.56 mmol) and AIBN (0.10 g) in cyclohexane (300 mL) and reflux for 6 hours. Cool to ambient temperature and concentrate in vacuo. Chromatograph on silica gel elute first with 3/97 ethyl acetate/hexane and then with 1/9 ethyl acetate/hexane to give 16.22 g of the title compound as a clear oil.

EXAMPLE 24

Scheme C, step c: (E) and (Z)-4-(p-Methoxybenzyloxy)-2-hydroxymethyl-1-fluorobut-1-ene Combine (E) and (Z)-4-(p-methoxybenzyloxy)-2-(t-butyldimethylsilyloxymethyl)-1-fluoro-1-tri-n-butylstannylbut-1-ene (7.73 g, 12.0 mmol) and THF (20 mL) and cool to 5° C. Slowly add tetrabutylammonium fluoride (13.2 mL, IM in THF, 13.2 mmol). Stir in the ice bath for 10 minutes then warm to room temperature and stir for 1 hour. Evaporate in vacuo and chromatograph on silica gel eluting with 2/3 ethyl acetate/hexane to give the title compound.

EXAMPLE 25

Scheme C, steps d : (E) and (Z)-4-(p-Methoxybenzyloxy)-2-benzoyloxymethyl-1-fluorobut-1-ene Combine (E) and (Z)-4-(p-methoxybenzyloxy)-2-hydroxymethyl-1-fluorobut-1-ene (3.43 g, 14.3 mmol) and benzoyl chloride (1.83 mL, 15.7 mmol) in pyridine (15 mL) and stir for 16 hours. Dilute the reaction mixture with 1/9 ethyl acetate/hexane (75 mL) and filter. Wash the filter cake with 1/9 ethyl acetate/hexane (25 mL) and extract the filtrate with saturated sodium bicarbonate solution. Dry over MgSO$_4$, filter and concentrate in vacuo. Remove residual pyridine under high vacuum at 50° C. Chromatograph on silica gel eluting with 1/9 ethyl acetate/hexane to give the title compound as an oil.

EXAMPLE 26

Scheme C, step e : (E) and (Z)-4-Hydroxy-2-benzoyloxymethyl-1-fluorobut-1-ene

Combine (E) and (Z)-4-(p-methoxybenzyloxy)-2-benzoyloxymethyl-1-fluorobut-1-ene (4.69 g, 14.98 mmol), methylene chloride (16 mL) and water (1 mL). Add 2,3-dichloro-5,6-dicyano-1,4-benzoquinone (3.4 g, 14.98 mmol) with rapid stirring. After 1.5 hours filter the reaction mixture and wash the filtrate three times with water, dry the organic layer over $MgSO_4$, filter and concentrate in vacuo.

Chromatograph on silica gel eluting with 1/2 ethyl acetate/hexane to give, 1.60 g of the (E)-isomer: $R_f$=0.29; silica gel, 1/2 ethyl acetate/hexane and 0.88 g of the (Z)-isomer: $R_f$=0.20; silica gel, 1/2 ethyl acetate/hexane, of the title compound.

EXAMPLE 27

Scheme C, step e: (Z)-4,5-Dihydroxy-2-benzoyloxymethyl-1-fluoropent-1-ene

Combine (Z)-4,5-dihydroxy-2-benzoyloxymethyl-1-fluoropent-1-ene-4,5-acetonide (50 mmol) with 80% aqueous acetic acid (250 mL) and stir at ambient temperature for six hours. Concentrate in vacuo and chromatograph the residue on silica gel to give the title compound.

EXAMPLE 28

Scheme C, Optional step f: (Z)-4-Hydroxy-2-benzoyloxymethyl-5-(t-butyldimethylsilyloxy)-1-fluoropent-1-ene Combine (Z)-4,5-dihydroxy-2-benzoyloxymethyl-1fluoropent-1-ene (30 mmol) with DMF (100 mL) and cool in an ice bath. Add t-butyldimethylsilyl chloride (33 mmol), triethylamine (45 mmol) and 4-dimethylaminopyridine (7.5 mmol). Stir the mixture in the ice bath for 5 minutes and then warm to ambient temperature and stir for sixteen hours. Partition the reaction mixture between diethyl ether and water. Separate the aqueous layer and extract twice with diethyl ether. Combine the organic layers, wash with water and saturated sodium chloride solution, dry over $MgSO_4$ and concentrate in vacuo. Chromatograph on silica gel to give the title compound.

Scheme D illustrates the preparation of structure 1 starting materials for Scheme A which afford compounds of Formula I in which $X_1$ and $X_2$ are hydrogen, fluorine, chlorine, chlorine and hydrogen, and hydrogen and chlorine. All the substituents, unless otherwise indicated, are previously defined. The reagents and starting materials are readily available to one of ordinary skill in the art.

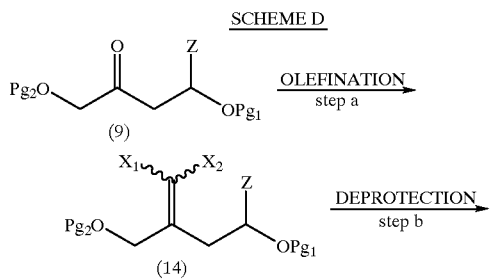

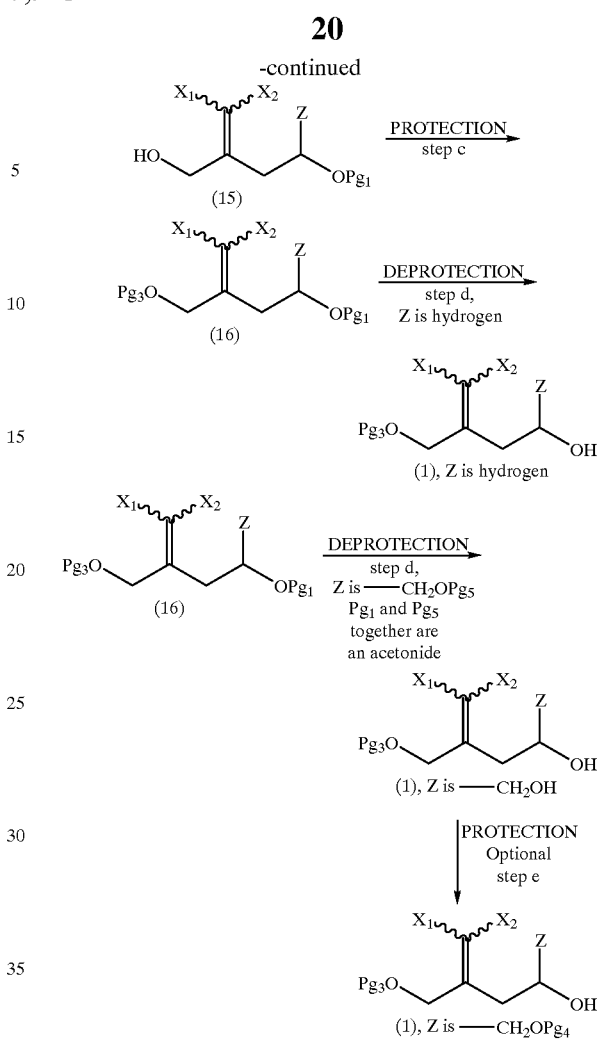

In Scheme D step a, ketone 9 undergoes an olefination reaction with a phosphorous ylide to give olefin 14.

Phosphorus ylides can be prepared according to procedures which are well known and appreciated in the art of chemistry such as those described by J. March in "Advanced Organic Chemistry: Reactions, Mechanisms and Structure", McGraw-Hill Book Company, 702-10 (1968); M. L. Edwards et al, *Tet Let* 31, 5571–5574, (1990); A. J. Speziale and K. W. Ratts, *JACS* 84, 855–859, (1962).

For example, a phosphorus ylide can be prepared by treatment of an appropriate phosphorane or phosphonate derivative with an appropriate base. A wide variety of bases can be used including alkoxides and organometallics, such as alkyllithium or lithium dialkylamide. The reaction is carried out in a solvent, such as tetrahydrofuran, benzene, toluene, or diethyl ether. The reaction is carried out at temperatures ranging from −60° C. to the reflux temperature of the solvent. The temperature that is used depends on the olefin forming phosphorous ylide used as is well known and appreciated in the art. The olefin 14 can be isolated and purified by techniques well known in the art, such as evaporation, extraction, chromatography, and recrystallization.

In Scheme D step b, the olefin 14 is deprotected by removal of protecting group $Pg_2$ to give the olefin alcohol of structure 15.

The removal of protecting groups is well known in the art. The procedure used depends on the protecting groups used in olefin of structure 14 as described in *Protecting Groups in*

*Organic Synthesis* by T. Greene. Olefin alcohol of structure 15 can be isolated and purified by techniques well known in the art, such as evaporation, extraction, chromatography, and recrystallization.

In Scheme D step c, the reactive hydroxyl of olefin alcohol 15 is protected to give protected olefin of structure 16.

For example, olefin alcohol 15 is contacted with a suitable protecting group forming reagent. The reaction is typically carried out in a solvent at a temperature between −60° C. and the refluxing temperature of the solvent. The selection and use of protecting groups as described in *Protecting Groups in Organic Synthesis* by T. Greene is well known and appreciated by those skilled in the art. The protected olefin of structure 16 can be isolated and purified by techniques well known in the art, such as extraction, chromatography, and recrystallization.

In Scheme D step d, for protected olefin of structure 16, in which Z is hydrogen, the protecting group $Pg_1$ is removed to give olefin of structure 1 in which Z is hydrogen to be use in preparing compounds of Formula I and II in which R is hydrogen.

The removal of protecting groups in a selective manner utilizing suitable protecting groups such as those described in *Protecting Groups in Organic Synthesis* by T. Greene is well known and appreciated by those skilled in the art. Compounds of structure 1 are isolated and purified by techniques well known in the art, such as extraction, chromatography, and recrystallization.

In Scheme D step d, for protected olefin of structure 16 in which Z is a protected hydroxymethyl group, —$CH_2OPg_5$, the protecting groups $Pg_1$ and $Pg_5$ are together an acetonide, the deprotection gives olefin diol of structure 1 in which Z is a hydroxymethyl —$CH_2OH$, a primary hydroxyl group.

For example, compound of structure 16 in which Z is a protected hydroxymethyl group, —$CH_2OPg_5$, the protecting groups $Pg_1$ and $Pg_5$ are together an acetonide, is contacted with a suitable aqueous acid, such as acetic acid, for 1 hour to 24 hours. The product of structure 1 in which Z is a hydroxymethyl group, −$CH_2OH$, is isolated and purified by techniques well known in the art. For example, concentrating the reaction mixture in vacuo and purifying the residue obtained by chromatography on silica gel.

In Scheme C Optional step e, the compound of structure 1 in which Z is a primary hydroxymethyl group, —$CH_2OH$, the primary hydroxyl group is selectively protected with a suitable protecting group forming reagent by techniques well known in the art and described in *Protecting Groups in Organic Synthesis* by T. Greene to be used to prepare compounds of the Formulas I and II in which R is hydroxymethyl. The compound of structure 1 in which Z is a protected hydroxymethyl, —$CH_2OPg_4$, is isolated and purified by techniques well known in the art, such as extraction, chromatography, and recrystallization.

The following examples present typical syntheses as described by Scheme D. These examples are understood to be illustrative only and is not intended to limit the scope of the present invention in any way. As used herein, the following terms have the meanings as indicated below: "g" refers to grams; "mL" refers to milliliters; "mg" refers to milligrams; "mmol" refers to millimoles; "° C." refers to degrees Celsius; "µL" refers to microliters; "THF" refers to tetrahydrofuran; "mp" refers to melting point; "M" refers to molar concentration; "$R_f$" refers to retention factor.

EXAMPLE 29

Scheme D, step a: (E) and (Z)-4-(p-Methoxybenzyloxy)-2-(t-butyldimethylsilyloxymethyl)-1-chlorobut-1-ene Combine (chloromethyl)triphenylphosphonium chloride (11.7 g, 33.8 mmol) with THF (100 mL) and cool to −60° C. during the addition of a THF solution of lithium hexamethyldisilazide (37.0 mL, 36.9 mmol). After the addition is complete remove the cooling bath and allow the reaction mixture to warm to −10° C. and maintain that temperature by placing the vessel in an ice/salt bath. Stir for 1 hour and add 4-(p-methoxybenzyloxy)-1-(t-butyldimethylsilyloxy)butan-2-one (10.4 g, 30.7 mmol) in THF (20 mL) and stir for 3 hours while warming to 0° C. Quench the reaction with saturated ammonium chloride solution and partition it between diethyl ether and water, wash the organic layer 2X with water 1X with saturated sodium chloride solution. Dry over $MgSO_4$ and concentrate in vacuo to give a solid. Dissolve the solid in ethyl acetate and wash with water, dry over $MgSO_4$ and concentrate in vacuo. Chromatograph on silica gel eluting with 1/19 ethyl acetate/hexane to give 10.5 g of the title compound as an oil. $R_f$=0.40; silica gel, 1/19 ethyl acetate/hexane.

EXAMPLE 30

Scheme D, step a: 4-(p-Methoxybenzyloxy)-2-(t-butyldimethylsilyloxymethyl)but-1-ene Combine methlytriphenylphosphonium bromide (3.08 g, 8.61 mmol) with THF (50 mL) and add a hexane solution of n-butyllithium (3.8 mL, 2.5 M, 9.47 mmol). After the addition is complete stir at ambient temperature for 0.5 hour. Add 4-(p-methoxybenzyloxy)-1-(t-butyldimethylsilyloxy)butan-2-one (2.65 g, 7.82 mmol) in THF (10 mL) and stir for 0.5 hours. Quench the reaction with saturated ammonium chloride solution and partition it between diethyl ether and water, wash the organic layer with water and then with saturated sodium chloride solution. Dry over $MgSO_4$ and concentrate in vacuo to give a residue. Chromatograph the residue on silica gel eluting with 1/19 ethyl acetate/hexane to give the title compound as an oil. $R_f$=0.25; silica gel, 1/9 ethyl acetate/hexane. $^1$H NMR ($CDCl_3$, 300 MHz) δ0.05 (s, 6H), 0.91 (s, 9H) 2.33 (t, J=6.98 Hz, 2H), 3.56 (t, J=6.98 Hz, 2H), 3.81 (s, 3H), 4.08 (s, 2H), 4.45 (s, 2H), 4.87 (s, 1H), 5.09 (d, J=1.65 Hz, 2H), 6.88 (d, J=8.73 Hz, 2H), 7.25 (d, J=8.73 Hz, 2H).

EXAMPLE 31

Scheme D, step b: (E) and (Z)-4-(p-Methoxybenzyloxy)-2-hydroxymethyl-1-chlorobut-1-ene Combine (Z)-4-(p-methoxybenzyloxy)-2-(t-butyldimethylsilyloxymethyl)-1-chlorobut-1-ene (5.00 g, 13.5 mmol) with THF (50 mL) and add a solution of tetrabutylammonium fluoride (15 mL, 1M, 15.0 mmol). After 0.5 hours dilute the reaction mixture with diethyl ether (100 mL) wash 3X with water and 1X with saturated sodium chloride solution. Dry the organic layer over $MgSO_4$ and concentrate in vacuo to give a oil. Chromatograph on silica gel eluting with 1/2 ethyl acetate/hexane to give the title compound. $R_f$=0.37, silica gel, 1/2 ethyl acetate/hexane; and $R_f$=0.30, silica gel, 1/2 ethyl acetate/hexane.

EXAMPLE 32

Scheme D, step b: 4-(p-Methoxybenzyloxy)-2-hydroxymethylbut-1-ene

Combine 4-(p-methoxybenzyloxy)-2-(t-butyldimethylsilyloxymethyl)but-1-ene (1.5 g, 4.75 mmol) and a solution of tetrabutylammonium fluoride (4.75 mL, 1M, 4.75 mmol). After 2.5 hours chromatograph on silica gel eluting with 1/2 ethyl acetate/hexane to give the title compound; $R_f$=0.24, silica gel, 1/2 ethyl acetate/hexane.

EXAMPLE 33

Scheme D, step c: (E) and (Z)-4-(p-Methoxybenzyloxy)-2-benzoyloxymethyl-1-chlorobut-1-ene Combine (Z)-4-(p-methoxybenzyloxy)-2-hydroxymethyl-1-chlorobut-1-ene (4.85 g, 18.89 mmol) with pyridine (20 mL) and add dropwise benzoyl chloride (2.63 mL, 22.27 mmol). Stir the mixture at ambient temperature for 16 hours. Dilute the reaction mixture with diethyl ether (100 mL) and washed 4X with saturated sodium bicarbonate solution, dry over $MgSO_4$ and concentrate in vacuo. Chromatograph on silica gel eluting with 1/9 ethyl acetate/hexane to give the separate geometric isomers of the title compound as an oil. (Z)-4-(p-Methoxybenzyloxy)-2-benzoyloxymethyl-1-chloro-but-1-ene: $R_f$=0.18, silica gel, 1/9 ethyl acetate/hexane; (E)-4-(p-Methoxybenzyloxy)-2-benzoyloxymethyl-1-chloro-but-1-ene: $R_f$=0.23, silica gel, 1/9 ethyl acetate/hexane.

EXAMPLE 34

Scheme D, step c: 4-(p-Methoxybenzyloxy)-2-benzoyloxymethylbut-1-ene

Combine 4-(p-methoxybenzyloxy)-2-hydroxymethylbut-1-ene (0.77 g, 3.46 mmol) with pyridine (3 mL) and add dropwise benzoyl chloride (603 μL, 5.2 mmol). Stir the mixture at room temperature for 20 hours. Dilute the reaction mixture with diethyl ether (100 mL) and washed 3X with saturated sodium bicarbonate solution, dry over $MgSO_4$ and concentrate in vacuo. Chromatograph on silica gel eluting with 1/9 ethyl acetate/hexane to give the title compound as an oil. $R_f$=0.28, silica gel, 1/9 ethyl acetate/hexane.

EXAMPLE 35

Scheme D, step d: (E)-4-Hydroxy-2-benzoyloxymethyl-1-chlorobut-1-ene

Combine (E)-4-(p-methoxybenzyloxy)-2-benzoyloxymethyl-1-chlorobut-1-ene (1.02.6 g, 7.18 mmol) with methylene chloride (16 mL) and water (1 mL) and stir rapidly. Add 2,3-dichloro-5,6-dicyano-1,4-benzoquinone (1.79 gm, 7.90 mmol). After 2 hours, filter the reaction mixture, rinse the filter cake with methylene chloride (200 mL) and concentrate the filtrate in vacuo. Chromatograph on silica gel eluting with 1/2 ethyl acetate/hexane to give the title compound as an oil. $R_f$=0.25; silica gel, 1/2 ethyl acetate/hexane.

EXAMPLE 36

Scheme D, step d: 4-Hydroxy-2-benzoyloxymethylbut-1-ene

Combine 4-(p-methoxybenzyloxy)-2-benzoyloxymethylbut-1-ene (1.08 g, 3.30 mmol) with methylene chloride (10 mL) and water (0.5 mL) and stir rapidly. Add 2,3-dichloro-5,6-dicyano-1,4-benzoquinone (0.826 gm, 3.64 mmol). After 0.25 hours filter the reaction mixture and rinse the filter cake with methylene chloride (20 mL) and concentrate the filtrate in vacuo. Chromatograph on silica gel eluting with 1/9 ethyl acetate/hexane to give the title compound as an oil. $R_f$=0.28; silica gel, 1/9 ethyl acetate/hexane.

EXAMPLE 37

Scheme D, step d: (Z)-4,5-Dihydroxy-2-benzoyloxymethyl-1-fluoropent-1-ene

Combine (Z)-4,5-dihydroxy-2-benzoyloxymethyl-1-fluoropent-1-ene-4,5-acetonide (10 mmol) with 80% aqueous acetic acid (25 mL) and stir at ambient temperature for six hours. Concentrate in vacuo and chromatograph the residue on silica gel to give the title compound.

EXAMPLE 38

Scheme D, Optional step e: (Z)-4-Hydroxy-2-benzoyloxymethyl-5-(t-butyldimethylsilyloxy)-1-fluoropent-1-ene Combine (Z)-4,5-dihydroxy-2-benzoyloxymethyl-1-fluoropent-1-ene (5 mmol) with DMF (20 mL) and cool in an ice bath before adding t-butyldimethylsilyl chloride (5.5 mmol), triethylamine (7.5 mmol) and 4-dimethylaminopyridine (0.5 mmol). Stir the mixture in the ice bath for 5 minutes and then allow to warm to ambient temperature and stir for sixteen hours. Partition the reaction mixture between diethyl ether and water. Separate the aqueous layer and wash twice with ether. Combine the organic layers wash with water and saturated sodium chloride solution, dry over $MgSO_4$ and concentrate in vacuo. Chromatograph on silica gel to give the title compound.

The preparation of compounds of structure 5 used as starting material for Scheme B is illustrated in Scheme E. All the substituents, unless otherwise indicated, are previously defined. The reagents and starting materials are readily available to one of ordinary skill in the art.

In Scheme E step a, α-lithiovinyltrimethylsilane is

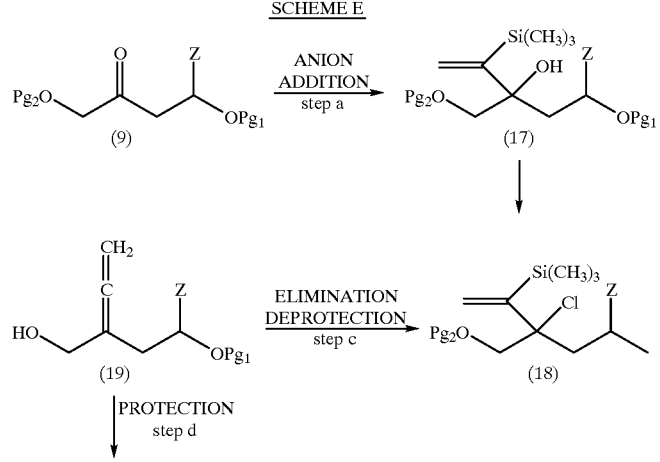

-continued

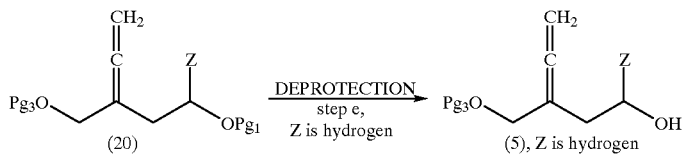

added to the ketone of structure 9 to give β-hydroxysilane of structure 17.

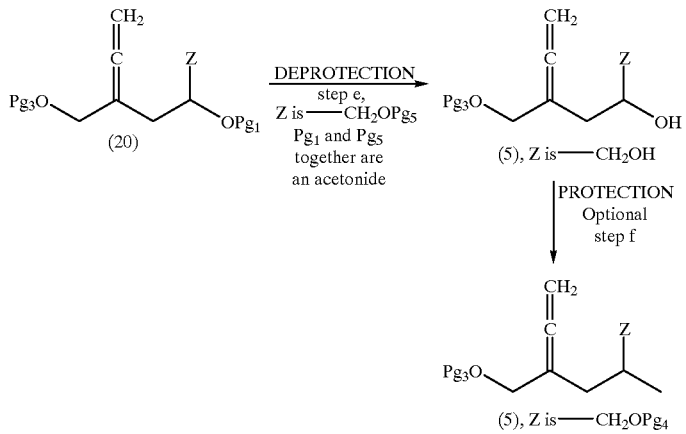

This anion addition reaction is well known in the art [T. H. Chan et al; JOC 43, 1526–1532, (1978)]. The anion is generated by the addition of t-butyllithium to α-bromovinyltrimethylsilane in diethy ether at −78° C., as described in the paper cited above. A equivalent molar amount of ketone 9 in a diethyl ether solution is added and the reaction is stirred for 1 hour maintaining the temperature at −78° C. and is then warmed to room temperature and stirred for from 1–24 hours. The product is isolated by quenching with water and extraction with diethyl ether, the organic layer is dried over magnesium sulfate and evaporated in vacuo to give β-hydroxysilane of structure 17. The compounds of structure 17 can be used in Scheme E step b, as isolated above or purified by chromatography on silica gel.

In Scheme E step b, β-hydroxysilane of structure 17 is chlorinated to give D-chlorosilane of structure 18. The chlorination reaction is carried out in a solvent, such as diethyl ether, carbon tetrachloride, or dichloromethane by adding a slight excess of a chlorinating agent, such as thionyl chloride to a solution of β-hydroxysilane of structure 17 with cooling with an ice bath if needed to maintain the temperature of the reaction at room temperature. The reaction mixture is stirred for 2–24 hours and the β-chlorosilane of structure 17 can be isolated by evaporation in vacuo. The compounds of structure 17 can be used in Scheme E step c, as isolated above or purified by recrystallization, chromatography on silica gel, or by distillation in vacuo.

In Scheme E step c, β-chlorosilane of structure 18 undergoes an elimination reaction and a deprotection to give allene of the structure 19. This step is carried out at room temperature in a suitable solvent, such as dimethyl sulfoxide or acetonitrile and a suitable anhydrous source of fluoride ion, such as tetraethylammonium fluoride, tetrabutylammonium fluoride, potassium fluoride, or cesium fluoride. The reaction mixture is stirred for 2 to 24 hours. The allene 20 can be isolated by pouring the reaction mixture into water and extraction using a suitable organic solvent, such as ethyl acetate, dichloromethane, or diethyl ether, drying over magnesium sulfate and evaporation in vacuo. Allene of structure 19 are purified using techniques well known in the art, such as chromatography and recrystallization.

In Scheme E step e, allene of structure 20 in which Z is hydrogen is deprotected as is well known and appreciated in the art and described in *Protecting Groups in Organic Synthesis* by T. Greene and is used to prepare compounds of Formulas I and II in which R is hydrogen.

For compound of structure 20 in which Z is a protected hydroxymethyl group, —CH$_2$OPg$_5$, the protecting groups Pg$_1$ and Pg$_5$ are together an acetonide, the deprotection gives allene diol of structure 5 in which Z is a hydroxymethyl —CH$_2$OH, a primary hydroxyl group.

For example, compound of structure 20 in which Z is a protected hydroxymethyl group, —CH$_2$OPg$_5$, the protecting groups Pg$_1$ and Pg$_5$ are together an acetonide, is contacted with a suitable aqueous acid, such as acetic acid, for 1 hour to 24 hours. The allene of structure 5 in which Z is a hydroxymethyl group, —CH$_2$OH, is isolated and purified by techniques well known in the art. For example, concentrating the reaction mixture in vacuo and purifying the residue obtained by chromatography on silica gel.

In Scheme E Optional step F, the allene of structure 5 in which Z is a primary hydroxymethyl group, —CH$_2$OH, the primary hydroxyl group is selectively protected with a suitable protecting group forming reagent by techniques well known in the art and described in *Protecting Groups in Organic Synthesis* by T. Greene and is used to prepare compounds of the Formulas I and II in which R is hydroxymethyl. The allene of structure 5 in which Z is a protected hydroxymethyl, —CH$_2$OPg$_4$, is isolated and purified by techniques well known in the art, such as extraction, chromatography, and recrystallization.

The following example presents a typical synthesis as described by Scheme E. This example is understood to be illustrative only and is not intended to limit the scope of the present invention in any way. As used herein, the following terms have the meanings as indicated below: "g" refers to grams; "mL" refers to milliliters; "mg" refers to milligrams; "mmol" refers to millimoles; "° C." refers to degrees Celsius.

EXAMPLE 39

Scheme E, step a: 5-(p-Methoxybenzyloxy)-3-(t-butyldimethylsilyloxy)-2-hydroxy-2-[(trimethyl)silyl]pent-1-ene Combine α-bromovinyltrimethylsilane (50.0 mmol) and anhydrous diethyl ether (150 mL) and cool to −78° C. Add slowly t-butyllithium (50.0 mmol) and stir at −78° C. for 2 hours. Add a solution of (p-methoxybenzyloxy)-1-(t-butyldimethylsilyloxy)butan-2-one (50.0 mmol) in anhydrous diethyl ether (10 mL) and stir at for 1 hour before warming to room temperature. After 4 hours add water and separate the layers, dry the organic layer over $MgSO_4$ and concentrate in vacuo to give a residue which is taken to the next step without further purification.

EXAMPLE 40

Scheme E, step b: 5-(p-Methoxybenzyloxy)-3-(t-butyldimethylsilyloxy)-2-chloro-2-[(trimethyl)silyl]pent-1-ene Combine the residue obtained above and carbon tetrachloride (40 mL). Add thionyl chloride (60.0 mmol, 1.2 equivalents) using an ice bath to keep the temperature of the reaction at or slightly below room temperature. Stir the reaction mixture for 4 hours and evaporate in vacuo to give a residue which is taken to the next step without further purification.

EXAMPLE 41

Scheme E, step c: 5-(p-Methoxybenzyloxy)-3-hydroxymethylpent-1,2-diene

Combine the residue obtained above and dimethyl sulfoxide (50 mL). Add anhydrous cesium fluoride (125 mmol, 2.5 equivalents) and stir for 18 hours. Partition the reaction mixture between water and diethyl ether and extract the aqueous layer with diethyl ether. Combine the organic layers and extract two times with water, dry over $MgSO_4$ and concentrate in vacuo. Chromatograph to give the title compound.

EXAMPLE 42

Scheme E, step d: 5-(p-Methoxybenzyloxy)-3-benzoyloxymethylpent-1,2-diene

Combine 5-(p-methoxybenzyloxy)-3-hydroxymethylpent-1,2-diene (25.0 mmol) and benzoyl chloride (25.0 mmol) in pyridine (25 mL) and stir for 16 hours. Partition the reaction mixture between diethyl ether and water, wash the organic layer 3X with saturated sodium bicarbonate and 1X with water, dry over $MgSO_4$ and concentrate in vacuo. Chromatograph on silica gel to give the title compound.

EXAMPLE 43

Scheme E, step e: 5-Hydroxy-3-benzoyloxymethylpent-1,2-diene

Combine 5-(p-methoxybenzyloxy)-3-benzoyloxymethylpent-1,2-diene (12.0 mmol), methylene chloride (25 mL) and water (1.25 mL). Add 2,3-dichloro-5,6-dicyano-1,4-benzoquinone (12.5 mmol) with rapid stirring. After 1.5 hours filter the reaction mixture and extract the filtrate three times with water, dry over $MgSO_4$ and concentrate in vacuo. Chromatograph on silica gel to give the title compound.

EXAMPLE 44

Scheme E, step e: 5,6-Dihydroxy-3-benzoyloxymethylhex-1,2-diene

Combine 5,6-dihydroxy-3-benzoyloxymethylhex-1,2-diene-5,6-acetonide (10 mmol) with 80% aqueous acetic acid (25 mL) and stir at ambient temperature for six hours. Concentrate in vacuo and chromatograph the residue on silica gel to give the title compound.

EXAMPLE 45

Scheme E, Optional step f: 5-Hydroxy-3-benzoyloxymethyl-6-(t-butyldimethylsilyloxy)hex-1,2-diene Combine 5,6-dihydroxy-3-benzoyloxymethylhex-1,2-diene (5 mmol) with DMF (20 mL) and cool in an ice bath before adding t-butyldimethylsilyl chloride (5.5 mmol), triethylamine (7.5 mmol) and 4-dimethylaminopyridine (0.5 mmol). Stir the mixture in the ice bath for 5 minutes and then allow to warm to ambient temperature and stir for sixteen hours. Partition the reaction mixture between diethyl ether and water. Separate the aqueous layer and wash twice with ether. Combine the organic layers wash with water and saturated sodium chloride solution, dry over $MgSO_4$ and concentrate in vacuo. Chromatograph on silica gel to give the title compound.

In Scheme F the preparation of ketone 9 in which Z is hydrogen is illustrated. All the substituents, unless otherwise indicated, are previously defined. The reagents and starting materials are readily available to one of ordinary skill in the art.

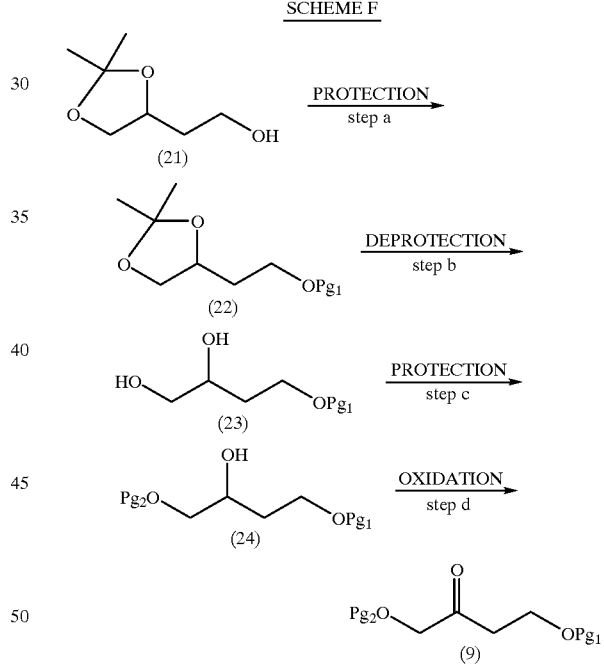

SCHEME F

In Scheme F step a, the reactive hydroxy of 1,2,4-butanetriol-1,2-acetonide (21) [K. Mori, T. Takigawa, and T. Matsuo; *Tetrahedron* 35, 933–940 (1979)] is protected with a standard protecting group well known in the art.

For example, 1,2,4-butanetriol-1,2-acetonide, (21), is added dropwise to stirred suspension of sodium hydride in a suitable organic solvent, such as dimethylformamide, and stirred for 30 minutes to 6 hours. A suitable protecting group forming reagent is added and the reaction mixture is stirred for 30 minutes to 24 hours before it is quenched by the addition of a suitable quenching agent, such as ammonium chloride. The product is isolated by techniques well known in the art, such as extraction with a suitable organic solvent, such as diethyl ether, ethyl acetate, or dichloromethane. The organic layer is dried over a suitable drying agent, such as magnesium sulfate, filtered and concentrated. The residue is then purified by techniques well known in the art. For example, the residue can be purified by chromatography and recrystallized to give acetonide of structure 22.

In Scheme F, step b, the acetonide of structure 22 is deprotected to give diol of structure 23.

For example, acetonide of structure 22 is contacted with a suitable aqueous acid, such as acetic acid, formic acid, or hydrochloric acid, for 1 hour to 24 hours. The product is isolated by techniques well known in the art, such as concentrating the reaction mixture in uacuo and the residue obtained can be purified by chromatography to give diol of structure 23.

In Scheme F, step c, the primary hydroxy of a diol of structure 23 is protected with a suitable fluoride labile protecting group, such as t-butyldimethylsilyl, t-butyldiphenylsilyl, or triethylsilyl, with t-butyldimethylsilyl being the most preferred. This is carried out by methods well known in the art.

For example, diol of structure 23 is contacted with a suitable fluoride labile protecting group forming reagent, such as t-butydimethyllsilyl chloride, t-butyldiphenylsilyl chloride, or triethylsilyl chloride, the most preferred being t-butyldimethylsilyl chloride in the presence of a suitable base, such as triethylamine, diisopropylethylamine, or imidazole with triethylamine being preferred. The reaction is carried out in a suitable solvent, such as tetrahydrofuran, dimethylformamide, or dichloromethane with dimethylformamide being preferred. This reaction may be done in the presence of a catalyst, such as 4-dimethylaminopyridine. After the mixture is stirred 30 minutes to 24 hours the product can be isolated from the reaction mixture by extraction with a suitable organic solvent, such as diethyl ether or ethyl acetate. The organic layer is dried over a suitable drying agent, such as magnesium sulfate, filtered and concentrated. The residue is then purified by techniques well known in the art, such as chromatography to give alcohol of structure 24.

In Scheme F, step d, an alcohol 24 is oxidized to a ketone of structure 9.

For example, two molar equivalents of dimethyl sulfoxide are added dropwise to a solution of oxalyl chloride in dichloromethane, at approximately −60° C. After the addition is complete, the reaction is stirred for approximately two minutes. A molar equivalent of alcohol 24 as a solution in dichloromethane is added dropwise. After the addition is complete the reaction mixture is stirred for approximately forty minutes, then an excess of triethylamine is added. The reaction mixture is allowed to stir with warming to ambient temperature over 1 hour to 5 hours. The ketone of structure 9 is isolated by methods well known in the art.

For example, the reaction mixture is diluted with a suitable organic solvent, such as dichloromethane and extracted with water and saturated aqueous solution of sodium chloride. The organic layer is dried over a suitable drying agent, such as magnesium sulfate, filtered and concentrated to give ketone 9, used to prepare compounds of Formula I and II in which R is hydrogen.

The following example presents a typical synthesis as described by Scheme F. This example is understood to be illustrative only and is not intended to limit the scope of the present invention in any way. As used herein, the following terms have the meanings as indicated below: "L" refers to liters; "g" refers to grams; "DMF" refers to dimethylformamide; "DMSO" refers to dimethyl sulfoxide; "mL" refers to milliliters; "mg" refers to milligrams; "mmol" refers to millimoles; "° C." refers to degrees Celsius; "M" refers to molar; "mp" refers to melting point; "$R_f$" refers to retention factor.

EXAMPLE 46

Scheme F, step a: 4-(p-Methoxybenzyloxy)butan-1,2-diol-1,2-acetonide.

Add 1,2,4-butanetriol-1,2-acetonide ( 50.0 g, 471 mmol) dropwise as a solution in DMF (30 mL) to a suspension of sodium hydride (5.5 g, 60% in oil, 137.2 mmol) in DMF (50 mL). Stir for one hour. Add dropwise a solution of p-methoxybenzyl chloride (11.82 g, 75.47 mmol) in DMF (30 mL) and stir the mixture for sixteen hours. Quench by the addition of saturated ammonium chloride solution and partition between diethyl ether and water. Extract the aqueous layer with ether (3×200 mL) and combine the organic layers and extract with saturated sodium chloride (2X 100 mL). Dry over $MgSO_4$, filter and concentrate in vacuo to yield an oil. Chromatography on silica gel eluting with 1/9 ethyl acetate/hexane to give 18.0 g of the title compound as a yellow oil. $R_f$=0.17; silica gel, 1/9 ethyl acetate/hexane.

EXAMPLE 47

Scheme F, step b: 4-(p-Methoxybenzyloxy)butan-1,2-diol

Combine 4-(p-methoxybenzyloxy)-1,2-butantriol-1,2-acetonide (15.0 g, 56.3 imol) and 80% aqueous acetic acid (250 mL) at ambient temperature for six hours. Concentrate in vacuo and chromatograph the residue on silica gel eluting first with 1/9 ethyl acetate/hexane and then with 1/9 methanol/methylene chloride to give 12.4 g of the title compound as an oil. $R_f$=0.30; silica gel, 1/9 methanol/methylene chloride.

EXAMPLE 48

Scheme F, step c: 4-(p-Methoxybenzyloxy)-1-(t-butyldimethylsilyloxy)butan-2-ol

Combine 4-(p-methoxybenzyloxy)-1,2-butandiol (42.43 g, 187.5 mmol) with DMF (700 mL) and cool in an ice bath before adding t-butyldimethylsilyl chloride (31.1 g, 206 mmol), triethylamine (31.4 mL, 225 mmol), and 4-dimethylaminopyridine (5.8 g, 47 mmol). Stir the mixture in the ice bath for 5 minutes and then allow to warm to ambient temperature and stir for sixteen hours. Filter and wash the filter cake with diethyl ether. Separate the aqueous layer and extract twice with ether. Combine the organic layers extract with water and saturated sodium chloride solution, dry over $MgSO_4$, filter and concentrate in vacuo. Chromatograph on silica gel eluting with 2/8 ethyl acetate/hexane to give 51.4 g of the title compound the as an oil. $R_f$=0.25; silica gel, 2/8 ethyl acetate/hexane.

EXAMPLE 49

Scheme F, step d: 4-(P-Methoxybenzyloxy)-1-(t-butyldimethylsilyloxy)butan-2-one

Cool a solution of oxalyl chloride (10.1 mL, 2M in methylene chloride, 20.15 mmol) in methylene chloride (60 mL) to −78° C. and add DMSO (3.0 mL, 42.18 mmol) dropwise at a rate that maintains the temperature below −60° C. After fifteen minutes add dropwise 4-(p-methoxybenzyloxy)-1-(t-butyldimethylsilyloxy)butan-2-ol (5.28 g, 15.5 mmol) as a solution in methylene chloride (20 mL). Stir the reaction for forty minutes, then add triethylamine (8.9 mL, 63.29 mmol) and remove the cooling bath allowing the reaction to slowly warm to room temperature over 2.5 hours. Dilute the reaction mixture to 200 mL with methylene chloride, extract with water (2×100 mL), saturated sodium chloride (100 mL) and dry over $MgSO_4$. Concentration in vacuo gives 4.85 g of the title compound as a yellow oil. $R_f$=0.39; silica gel, 2/8 ethyl acetate/hexane.

In Scheme G the preparation of ketone 9 in which Z is a protected hydroxymethyl group is presented. All the substituents, unless otherwise indicated, are previously defined. The reagents and starting materials are readily available to one of ordinary skill in the art.

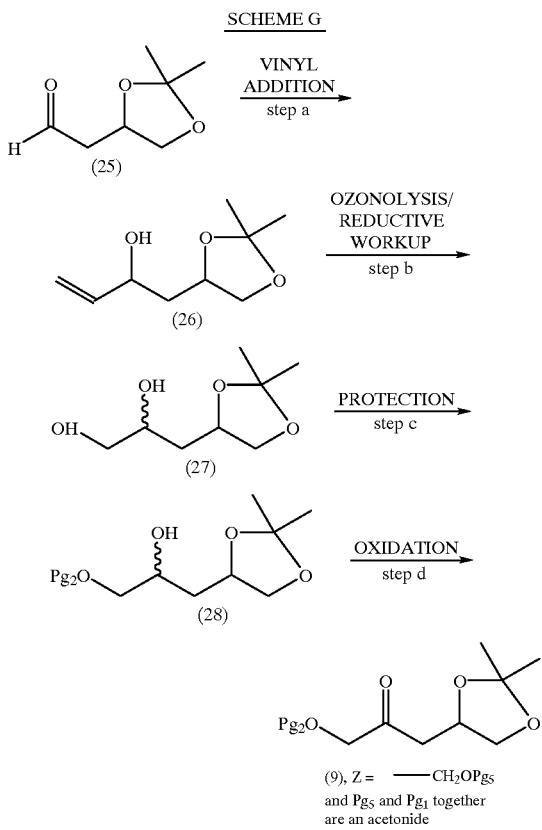

In Scheme G step a, aldehyde of structure 25 [F. E. Ziegler et al; JACS 115, 2581–2589, (1993)] undergoes the addition of a vinyl group to give allylic alcohol of structure 26.

For example, a solution of aldehyde 25 in anhydrous tetrahydrofuran is cooled to between 0° C. and −78° C. and a solution of vinylmagnesium bromide is added and the reaction mixture is stirred for 2 to 24 hours. The reaction is quenched with a saturated aqueous solution of ammonium chloride and the allylic alcohol 26 is isolated by extraction using a suitable organic solvent, such as diethyl ether or ethyl acetate. The organic layer is dried over magnesium sulfate, filtered, and concentrated in uacuo. The allylic alcohol of structure 26 can be purified using techniques well known in the art, such as chromatography or distillation.

In Scheme G step b, allylic alcohol 26 is ozonized with a reductive workup to give the diol of structure 27.

For example, allylic alcohol 26 in anhydrous dichloromethane is cooled to −40° C. and ozonized oxygen is passed through the solution until a persistent blue color is obtained. The solvent is evaporated in vacuo and the residue is dissolved in a suitable solvent, such as water, methanol, isopropanol, or ethanol or mixtures of the aforementioned alcohols and water and is contacted with a reducing agent, such as potassium borohydride, lithium borohydride, or sodium borohydride with sodium borohydride being preferred. The reaction mixture is stirred for from 1 to 12 hours and then is quenched with hydrochloric acid until the reaction is neutral and the solvents are evaporated in vacuo. The diol of structure 27 is isolated using techniques known in the art, such as extraction using a suitable organic solvent, such as dichloromethane, ethyl acetate, or diethyl ether. The organic layer is dried and evaporated in vacuo. The compound of structure 27 can be purified by chromatography and distillation.

In Scheme G, step c, the primary hydroxy of a diol of structure 27 is protected with a suitable fluoride labile protecting group, such as t-butyldimethylsilyl, t-butyldiphenylsilyl, or triethylsilyl to give alcohol of structure 28. This is carried out by methods well known in the art.

For example, diol of structure 27 is contacted with a suitable fluoride labile protecting group forming reagent, such as t-butyldimethylsilyl chloride, t-butyldiphenylsilyl chloride, or triethylsilyl chloride, with t-butyldimethylsilyl chloride being preferred. The reaction is carried out in the presence of a suitable base, such as triethylamine, diisopropyethyllamine, or imidazole with triethylamine being preferred. The reaction is carried out in a suitable solvent, such as tetrahydrofuran, dimethylformamide, or dichloromethane with dimethylformamide being preferred. This reaction may be done in the presence of a catalyst, such as 4-dimethylaminopyridine. After the mixture is stirred 30 minutes to 24 hours the product can be isolated from the reaction mixture by extraction with a suitable organic solvent, such as diethyl ether or ethyl acetate. The organic layer is dried over a suitable drying agent, such as magnesium sulfate, filtered and concentrated. The residue is then purified by techniques well known in the art, such as chromatography to give alcohol of structure 28.

In Scheme G, step d, an alcohol 28 is oxidized to the ketone of structure 9 in which Z is a protected hydroxymethyl group, —$CH_2OPg_5$, and $Pg_1$ and $Pg_5$ taken together are an acetonide.

For example, two molar equivalents of dimethyl sulfoxide are added dropwise to a solution of oxalyl chloride in dichloromethane, at approximately −60° C. After the addition is complete, the reaction is stirred for approximately two minutes. A molar equivalent of alcohol 26 as a solution in dichloromethane is added dropwise. After the addition is complete the reaction mixture is stirred for approximately forty minutes, then an excess of triethylamine is added. The reaction mixture is allowed to stir with warming to ambient temperature over 1 hour to 5 hours. The ketone of structure 9 is isolated by methods well known in the art. For example, the reaction mixture is diluted with a suitable organic solvent, such as dichloromethane and extracted with water and saturated aqueous solution of sodium chloride. The organic layer is dried over a suitable drying agent, such as magnesium sulfate, filtered and concentrated to give ketone 9 in which Z is a protected hydroxymethyl group, $OPg_5$, and $Pg_1$ and $Pg_5$ taken together are an acetonide.

The following example presents a typical synthesis as described by Scheme F. This example is understood to be illustrative only and is not intended to limit the scope of the present invention in any way. As used herein, the following terms have the meanings as indicated below: "g" refers to grams; "mL" refers to milliliters; "DMF" refers to dimethylformamide; "mmol" refers to millimoles; "° C." refers to degrees Celsius; "M" refers to molar.

EXAMPLE 50

Scheme G, step a: 3,5,6-trihydroxyhex-1-ene-5,6-acetonide

Combine 3,4-dihydroxybutan-1-al (F. E. Ziegler et al; JACS 115, 2581–2589, (1993)] (50 mmol) and anhydrous tetrahydrofuran (200 mL) and cool to −60° C. Add vinylmagnesium bromide (100 mmol, 2 equivalents) stir for 4 hours. Quench the reaction by the addition of a saturated aqueous solution of ammonium chloride. Extract with diethyl ether and dry the organic layer over $MgSO_4$ and concentrate in vacuo. Chromatography on silica gel to give the title compound.

EXAMPLE 51
Scheme G, step b: 1,2,4,5-tetrahydroxypentane-4,5-acetonide

Combine 3,5,6-trihydroxyhex-1-ene-5,6-acetonide (40 mmol) and anhydrous dichloromethane (200 mL) and cool to −40° C. Pass ozonized oxygen though the solution until a persistent light blue colored solution is obtained. Evaporate the solvent and redissolve the residue in ethanol and add sodium borohydride (80 mmol) and stir for 4 hours. Carefully add 3M hydrochloric acid solution until the reaction is neutral (pH=7.0). Evaporate to remove the ethanol and extract with dichloromethane. Dry the organic layer over $MgSO_4$, filter, and concentrate in vacuo. Chromatograph on silica gel to give the title compound.

EXAMPLE 52
Scheme G, step c: 1-(t-butyldimethylsilyl)oxy-2,4,5-trihydroxypentane-4,5-acetonide Combine 1,2,4,5-tetrahydroxypentane-4,5-acetonide (20 mmol) with DMF (100 mL) and cool in an ice bath before adding t-butyldimethylsilyl chloride (20 mmol), triethylamine (22 mmol) and 4-dimethylaminopyridine (0.1 mmol). Stir the mixture in the ice bath for 5 minutes and then allow to warm to ambient temperature and stir for sixteen hours. Partition the reaction mixture between diethyl ether and water. Separate the aqueous layer and wash twice with ether. Combine the organic layers wash with water and saturated sodium chloride solution, dry over $MgSO_4$ and concentrate in vacuo. Chromatograph on silica gel to give the title compound.

EXAMPLE 53
Scheme G, step d: 1-(t-butyldimethylsilyl)oxy-4,5-dihydroxypent-2-one-4,5-acetonide Cool a solution of oxalyl chloride (10.1 mL, 2M in methylene chloride, 20.15 mmol) in methylene chloride (60 mL) to −78° C. and add DMSO (3.0 mL, 42.18 mmol) dropwise at a rate that maintains the temperature below −60° C. After fifteen minutes add dropwise 1-(t-butyldimethylsilyl)oxy-2,4,5-trihydroxypentane-4,5-acetonide (15 mmol) as a solution in methylene chloride (20 mL). Stir the reaction for forty minutes, then add triethylamine (8.9 mL, 63.29 mmol) and remove the cooling bath allowing the reaction to slowly warm to room temperature over 2.5 hours. Dilute the reaction mixture to 200 mL with methylene chloride, wash with water (2×100 mL), saturated sodium chloride (100 mL) and dry over $MgSO_4$. Concentrate in vacuo and chromatograph on silica gel to give the title compound.

In a further embodiment, the present invention provides a method for the treatment of a patient afflicted with a neoplastic disease state comprising the administration thereto of a therapeutically effective antineoplastic amount of a compound of Formula I or II. The term "neoplastic disease state" as used herein refers to an abnormal state or condition characterized by rapidly proliferating cell growth or neoplasm. Neoplastic disease states for which treatment with a compound of Formula I or II will be particularly useful include: Leukemias such as, but not limited to, acute lymphoblastic, chronic lymphocytic, acute myeloblastic and chronic myelocytic; Carcinomas, such as, but not limited to, those of the cervix, breast, prostate, esophagus, stomach, small intestines, colon and lungs; Sarcomas such as, but not limited to, oesteroma, osteosarcoma, lipoma, liposarcoma, hemangioma and hemangiosarcoma; Melanomas, including amelanotic and melanotic; and mixed types of neoplasias such as, but not limited to carcinosarcoma, lymphoid tissue type, folicullar reticulum, cell sarcoma and Hodgkins Disease. Neoplastic disease states for which treatment with a compound of Formula I and II will be particularly preferred include: leukemias; solid tumors of the breast and prostrate, melanomas; and carcinomas of the colon and lung.

As used herein, the term "patient" refers to a warm-blooded animal, such as a human, which is afflicted with a particular neoplastic or viral disease state.

A therapeutically effective antineoplastic amount of a compound of Formula I or II refers to an amount which is effective, upon single or multiple dose administration to the patient, in controlling the growth of the neoplasm or in prolonging the survivability of the patient beyond that expected in the absence of such treatment. As used herein, "controlling the growth" of the neoplasm refers to slowing, interrupting, arresting or stopping its growth and metastases and does not necessarily indicate a total elimination of the neoplasm.

In addition, the present invention provides a method for the treatment of a patient afflicted with a viral infection comprising the administration thereto of a therapeutically effective antiviral amount of a compound of Formula I or II. The term "viral infection" as used herein refers to an abnormal state or condition characterized by viral transformation of cells, viral replication and proliferation. Viral infections for which treatment with a compound of the Formula I or II will be particularly useful include: Retroviruses such as, but not limited to, ETLV-I, ETLV-II, human immunodeficiency viruses, HTLV-III (AIDS virus), and the like; RNA viruses such as, but not limited to, influenza type A, B, and C, mumps, measles, rhinovirus, dengue, rubella, rabies, hepatitis virus A, encephalitis virus, and the like; DNA viruses such as, but not limited to, herpes, vaccinia, pappiloma virus (wart), hepatitis virus B, and the like.

A "therapeutically effective antiviral amount" of a compound of Formula I or II refers to an amount which is effective, upon single or multiple dose administration to the patient, in controlling the growth of the virus or in prolonging the survivability of the patient beyond that expected in the absence of such treatment. As used herein, "controlling the growth" of the virus refers to slowing, interrupting, arresting or stopping the viral transformation of cells or the replication and proliferation of the virus and does not necessarily indicate a total elimination of the virus.

As used herein, the term "therapeutically effective amount" refers to a therapeutically effective antineoplastic or antiviral amount of a compound of the Formula I or II. A therapeutically effective amount can be readily determined by the attending diagnostician, as one skilled in the art, by the use of known techniques and by observing results obtained under analogous circumstances. In determining the therapeutically effective amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

A therapeutically effective amount of a compound of Formula I or II is expected to vary from about 0.1 milligram per kilogram of body weight per day (mg/kg/day) to about 100 mg/kg/day. Preferred amounts are expected to vary from about 0.5 to about 10 mg/kg/day.

In effecting treatment of a patient afflicted with a disease state described above, a compound of Formula I or II can be administered in any form or mode which makes the compound bioavailable in effective amounts, including oral and parenteral routes. For example, compounds of Formula I or II can be administered orally, subcutaneously, intramuscularly, intravenously, transdermally, intranasally, rectally, and the like. Oral administration is generally preferred. One skilled in the art of preparing formulations can readily select the proper form and mode of administration depending upon the particular characteristics of the compound selected the disease state to be treated, the stage of the disease, and other relevant circumstances.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable acid addition salts for purposes of stability, convenience of crystallization, increased solubility and the like.

In another embodiment, the present invention provides compositions comprising a compound of Formula I or II in admixture or otherwise in association with one or more inert carriers. These compositions are useful, for example, as assay standards, as convenient means of making bulk shipments, or as pharmaceutical compositions. An assayable amount of a compound of Formula I or II is an amount which is readily measurable by standard assay procedures and techniques as are well known and appreciated by those skilled in the art. Assayable amounts of a compound of Formula I or II will generally vary from about 0.001% to about 75% of the composition by weight. Inert carriers can be any material which does not degrade or otherwise covalently react with a compound of Formula I or II. Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising a therapeutically effective amount of a compound of Formula I or II in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

As with any group of structurally related compounds which possesses a particular generic utility, certain groups and configurations are preferred for compounds of Formulas I and II in their end-use application.

With respect to the substituents $X_1$ and $X_2$, compounds of Formula I wherein $X_1$ is fluoro and $X_2$ is hydrogen, and those wherein $X_1$ is hydrogen and $X_2$ is fluoro, are generally preferred.

With respect to the substituent R, compounds of the Formulas I and II wherein R is hydrogen are generally preferred.

The following are additional preferred embodiments for compounds of Formulas I and II: compounds wherein V is oxy, compounds wherein $Y_1$ is a CH group, compounds wherein $Y_2$ is nitrogen, compounds wherein $Y_3$ is nitrogen and compounds wherein V is hydrogen, compounds wherein $Y_4$ is hydrogen, and compounds wherein $Y_5$ is amino are generally preferred.

The following list identifies compounds of the Formulas I and II which are particularly preferred embodiments of the present invention:

(E)-4-(Adenin-9-yl)-2-hydroxymethyl-1-fluorobut-1-ene,
(E)-4-(Cytosin-1-yl)-2-hydroxymethyl-1-fluorobut-1-ene,
(Z)-4-(Cytosin-1-yl)-2-hydroxymethyl-1-fluorobut-1-ene,
(Z)-4-(Adenin-9-yl)-2-hydroxymethyl-1-fluorobut-1-ene,
(E)-4-(Guanin-9-yl)-2-hydroxymethyl-1-fluorobut-1-ene,
(Z)-4-(Guanin-9-yl)-2-hydroxymethyl-1-fluorobut-1-ene,
4-(Adenin-9-yl)-2-hydroxymethylbut-1-ene, 4-(Adenin-9-yl)-2-hydroxymethyl-1,1-dichlorobut-1-ene, (E)-4-(Adenin-9-yl)-2-hydroxymethyl-1-chlorobut-1-ene, (Z)-4-(Adenin-9-yl)-2-hydroxymethyl-1-chlorobut-1-ene,
3-Hydroxymethyl-5-(urac-1-yl)pent-1,2-diene, 4-(Ctyosin-1-yl)-2-hydroxymethylbut-1-ene, 4-(Adenin-9-yl)-2-hydroxymethyl-1,1-difluorobut-1-ene, 4-(Cytosin-1-yl)-2-hydroxymethyl-1,1-difluorobut-1-ene.

The following example provides an illustration of the utility of the compounds of the present invention. This example is understood to be illustrative only and is not intended to limit the scope of the invention in any way.

EXAMPLE 54

INHIBITORY EFFECTS OF COMPOUNDS ON HeLa CELL PROLIFERATION

The inhibitory effect of various compounds of formula (1) on HeLa cell proliferation invitro was determined according to the method described by Sunkara et al. [*J. Natl. Cancer Instit.* 70, 505–509 (1983)]. Exponentially growing HeLa cells were incubated in the presence or absence of various concentrations of test compounds for 96 hours. $IC_{50}$ values were calculated which represent the test compound concentration at 50% inhibition of cell growth. The results of this study are presented in Table 1.

TABLE 1

INHIBITORY EFFECTS OF COMPOUNDS ON HeLa CELL PROLIFERATION

| Compound | Growth Inhibition $IC_{50}$, μg/mL |
|---|---|
| A | 0.25 |
| B | 1.0 |
| C | 0.6 |

Compound A = (E)-4-(Adenin-9-yl)-2-hydroxymethyl-1-fluorobut-1-ene
Compound B = (Z)-4-(Adenin-9-yl)-2-hydroxymethyl-1-fluorobut-1-ene
Compound C = 4-(Adenin-9-yl)-2-hydroxymethyl-1-but-1-ene

What is claimed is:

1. A compound of the formula (Formula I)

wherein $X_1$ and $X_2$ are each independently hydrogen, fluorine, or chlorine, with the proviso that $X_1$ and $X_2$ are not both hydrogen, R is hydrogen or hydroxymethyl, J is a radical of the formula $Y_1$ is a CH group, a CCl group, a CBr group or a $CH_2$ group, $Y_2$ and $Y_3$ are each independently nitrogen or a CH group, $Y_4$ is hydrogen, $C_1$–$C_4$ alkyl, $C_1$–$C_4$ alkoxy or halogen, $Y_5$ is $NH_2$ or $C_1$–$C_4$ alkoxy.

Q is $NH_2$, NHOH, $NHCH_3$— OH, or hydrogen, and

V is hydrogen, halogen or $NH_2$;

or a pharmaceutically acceptable salt thereof.

2. A compound according to claim 1 where $Y_1$ is a CH group.

3. A compound according to claim 2 wherein V is hydrogen.

4. A compound according to claim 3 wherein Q is $NH_2$.

5. A compound according to claim 4 wherein R is hydrogen.

6. A. compound according to claim 4 wherein $X_1$ and $X_2$ are fluorine.

7. A compound according to claim 4 wherein $X_1$ is fluorine and $X_2$ is hydrogen.

8. A compound according to claim 4 wherein $X_1$ is hydrogen and $X_2$ is fluorine.

9. A compound according to claim 4 wherein $X_1$ and $X_2$ are chlorine.

10. A compound according to claim 4 wherein $X_1$ is chlorine and $X_2$ is hydrogen.

11. A compound according to claim 4 wherein $X_1$ is hydrogen and $X_2$ is chlorine.

12. A compound according to claim 4 wherein $Y_5$ is $NH_2$.

13. A compound according to claim 12 wherein $Y_4$ is hydrogen.

14. A compound according to claim 13 wherein $X_1$ and $X_2$ are fluorine.

15. A compound according to claim 13 wherein $X_1$ is fluorine and $X_2$ is hydrogen.

16. A compound according to claim 13 wherein $X_1$ is hydrogen and $X_2$ is fluorine.

17. A compound according to claim 13 wherein $X_1$ and $X_2$ are chlorine.

18. A compound according to claim 13 wherein $X_1$ is chlorine and $X_2$ is hydrogen.

19. A compound according to claim 13 wherein $X_1$ is hydrogen and $X_2$ is chlorine.

20. A method of treating a patient afflicted with a solid tumors of the breast or prostrate, a melanoma, a carcinoma of the colon or lung or a leukemia comprising the administration thereto of a therapeutically effective amount of a compound of claim 1.

21. A method of controlling the growth of a solid tumor of the breast or prostate, a melanoma, a carcinoma of the colon or lung or a leukemia in a patient in need thereof comprising administration thereto of a therapeutically effective amount of a compound of claim 1.

22. A pharmaceutical composition comprising a therapeutically effective amount of a compound of claim 1 in admixture or otherwise in association with one or more pharmaceutically acceptable carriers or excipients.

23. The compound according to claim 1 wherein said compound is (E)-4-(Adenin-9-yl)-2-hydroxymethyl-1-fluorobut-1-ene.

24. The compound according to claim 1 wherein said compound is (Z)-1-(Adenin-9-yl)-2-hydroxymethyl-1-fluorobut-1-ene.

25. The compound according to claim 1 wherein said compound is (Z)-4-(Adenin-9-yl)-2-hydroxymethyl-1-chlorobut-1-ene.

26. The compound according to claim 1 wherein said compound is (Z)-4-(Adenin-9-yl)-2-hydroxymethyl-1-chlorobut-1-ene.

* * * * *